United States Patent
Morishima et al.

(10) Patent No.: US 10,930,385 B2
(45) Date of Patent: Feb. 23, 2021

(54) REPORT GENERATION SUPPORT APPARATUS AND REPORT READING APPARATUS

(71) Applicant: Toshiba Medical Systems Corporation, Otawara (JP)

(72) Inventors: Hiroshizu Morishima, Utsunomiya (JP); Maki Minakuchi, Utsunomiya (JP); Takafumi Yoshida, Yokohama (JP)

(73) Assignee: Canon Medical Systems Corporation, Otawara (JP)

(*) Notice: Subject to any disclaimer, the term of this patent is extended or adjusted under 35 U.S.C. 154(b) by 1249 days.

(21) Appl. No.: 14/483,984

(22) Filed: Sep. 11, 2014

(65) Prior Publication Data

US 2014/0379382 A1    Dec. 25, 2014

Related U.S. Application Data

(63) Continuation of application No. PCT/JP2013/056874, filed on Mar. 12, 2013.

(30) Foreign Application Priority Data

Mar. 12, 2012  (JP) .............................. JP2012-054131

(51) Int. Cl.
  *G06Q 50/24*   (2012.01)
  *G16H 15/00*   (2018.01)
  (Continued)

(52) U.S. Cl.
  CPC .............. *G16H 30/20* (2018.01); *G16H 15/00* (2018.01); *A61B 5/055* (2013.01); *A61B 5/743* (2013.01); *A61B 6/032* (2013.01); *A61B 6/463* (2013.01)

(58) Field of Classification Search
  CPC .................... G06Q 50/22; G06Q 50/24; G06F 19/322–327; G06K 9/00
  (Continued)

(56) References Cited

U.S. PATENT DOCUMENTS

| | | | | |
|---|---|---|---|---|
| 7,764,817 B2* | 7/2010 | Georgescu | ................ | G06T 7/12 382/128 |
| 7,945,083 B2* | 5/2011 | Zhang | .................... | G16H 30/20 382/132 |

(Continued)

FOREIGN PATENT DOCUMENTS

| | | |
|---|---|---|
| CN | 101546361 A | 9/2009 |
| CN | 101561848 A | 10/2009 |

(Continued)

OTHER PUBLICATIONS

Google patents search, May 8, 2019 (Year: 2019).*

(Continued)

*Primary Examiner* — Dilek B Cobanoglu
(74) *Attorney, Agent, or Firm* — Oblon, McClelland, Maier & Neustadt, L.L.P.

(57) ABSTRACT

The object of the present invention is to provide a report generation support apparatus and a report reading apparatus which are able to easily generate a diagnostic report. The report generation support apparatus of the embodiments comprises a display, a specifying part, and a generator. The display configures to display a diagnostic report and a first medical image. The specifying part configures to specify a predetermined region or a predetermined position in the first medical image displayed on the display. The generator configures to generate a second medical image, based on the predetermined region or position specified by the specifying part, as well as the first medical image.

32 Claims, 27 Drawing Sheets

(51) Int. Cl.
*G16H 30/20* (2018.01)
*A61B 6/03* (2006.01)
*A61B 5/00* (2006.01)
*A61B 5/055* (2006.01)
*A61B 6/00* (2006.01)

(58) Field of Classification Search
USPC .................................................. 382/128, 132
See application file for complete search history.

(56) References Cited

U.S. PATENT DOCUMENTS

| | | | |
|---|---|---|---|
| 8,199,985 B2* | 6/2012 | Jakobsson | G06K 9/6209 |
| | | | 382/128 |
| 2004/0085443 A1* | 5/2004 | Kallioniemi | G06K 9/00134 |
| | | | 348/135 |
| 2004/0151358 A1 | 8/2004 | Yanagita et al. | |
| 2007/0211930 A1* | 9/2007 | Dolwick | G06T 5/008 |
| | | | 382/132 |
| 2009/0076853 A1 | 3/2009 | Sagawa | |
| 2009/0087047 A1 | 4/2009 | Moriya | |
| 2009/0087048 A1* | 4/2009 | Takahashi | G06F 19/321 |
| | | | 382/128 |
| 2009/0087049 A1 | 4/2009 | Takahashi | |
| 2009/0208076 A1 | 8/2009 | Nakajima et al. | |
| 2009/0248441 A1 | 10/2009 | Okada | |
| 2009/0248447 A1 | 10/2009 | Niwa et al. | |
| 2009/0262995 A1 | 10/2009 | Futami et al. | |
| 2010/0034442 A1* | 2/2010 | Minakuchi | G06F 19/321 |
| | | | 382/128 |
| 2011/0066635 A1 | 3/2011 | Moriya | |
| 2011/0075913 A1 | 3/2011 | Moriya | |
| 2011/0144482 A1 | 6/2011 | Sendai et al. | |
| 2011/0218425 A1 | 9/2011 | Kusunoki | |

FOREIGN PATENT DOCUMENTS

| | | |
|---|---|---|
| CN | 101645111 A | 2/2010 |
| CN | 102138827 A | 8/2011 |
| JP | 8-38433 A | 2/1996 |
| JP | 09-198453 | 7/1997 |
| JP | 2002-28154 A | 1/2002 |
| JP | 2002-200048 A | 7/2002 |
| JP | 2004-187980 A | 7/2004 |
| JP | 2004-230001 A | 8/2004 |
| JP | 2008-006169 A | 1/2008 |
| JP | 2009-70201 A | 4/2009 |
| JP | 2009-82227 A | 4/2009 |
| JP | 2009-82465 A | 4/2009 |
| JP | 2009-86765 A | 4/2009 |
| JP | 2009-189541 A | 8/2009 |
| JP | 2009-230629 A | 10/2009 |
| JP | 2009-238037 A | 10/2009 |
| JP | 2010-015504 A | 1/2010 |
| JP | 2010-167144 A | 8/2010 |
| JP | 2010-237930 A | 10/2010 |
| JP | 2011-062283 A | 3/2011 |
| JP | 2011-092684 A | 5/2011 |
| JP | 2011-120747 A | 6/2011 |
| JP | 2011-182808 A | 9/2011 |

OTHER PUBLICATIONS

Google patents search, Dec. 11, 2019 (Year: 2019).*
ip.com search, Oct. 15, 2020 (Year: 2020).*
Combined Chinese Office Action and Search Report dated Jul. 4, 2016 in Patent Application No. 201380004578.8 (with English language translation of categories of cited documents).
Office Action dated May 30, 2017 in Japanese Patent Application No. 2013-049569.
International Search Report dated Jun. 18, 2013 for PCT/JP2013/056874 filed on Mar. 12, 2013 with English Translation.
Office Action dated Nov. 1, 2016 in Japanese Patent Application No. 2013-49569.

* cited by examiner

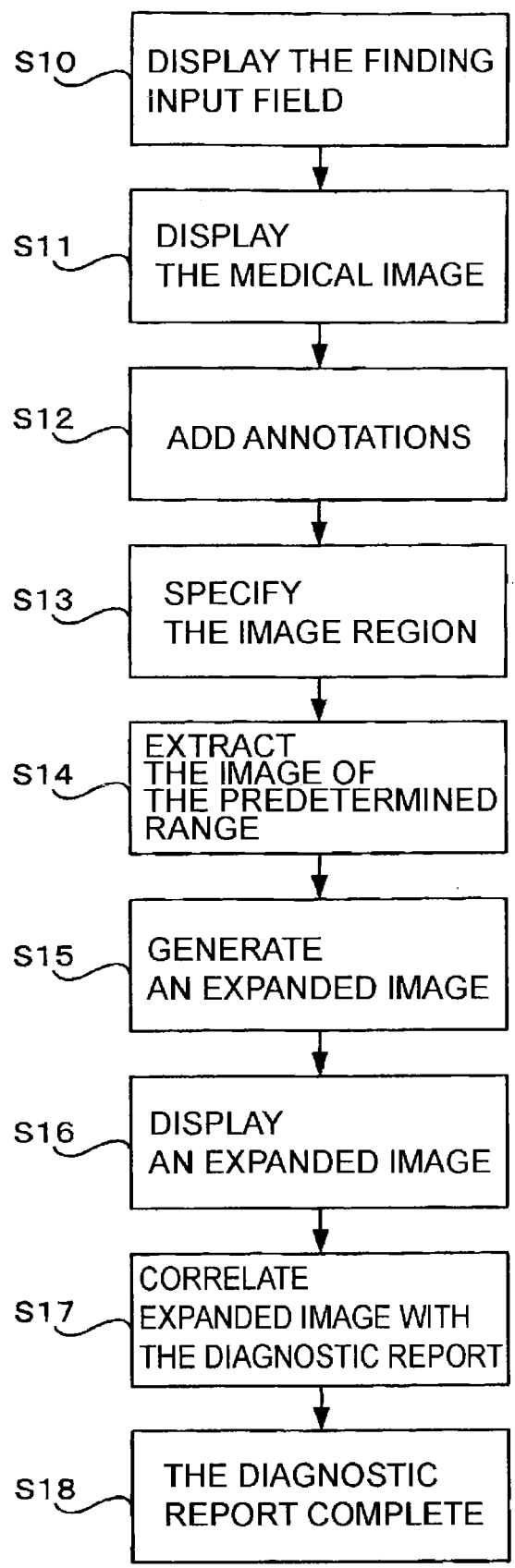

REPORT GENERATION SUPPORT APPARATUS AND REPORT READING APPARATUS

CROSS-REFERENCE TO RELATED APPLICATIONS

This application is based upon and claims the benefit of priority from Japanese Patent Applications No. 2012-054131, filed Mar. 12, 2012; the entire contents of all of which are incorporated herein by reference.

FIELD

The embodiments of the present invention relate to a report generation support apparatus and a report reading apparatus.

BACKGROUND

The medical industry is subdivided into specialized fields. Therefore, it is widely carried out to ask medical specialists (physicians) to interpret medical images obtained by medical imaging apparatuses (X-ray CT apparatus, MRI apparatus, and the like).

The physician performs, as checking medial images of interpret targets, collecting findings therefrom to generate a diagnostic report.

A report generation apparatus is used to generate the diagnostic report. In general, the physician checks the medial images displayed on a display of the report generation apparatus, and finds a finding to generate the diagnostic report. The physician then inputs the findings to a finding input field displayed on the display.

At this time, in order to clarify a part to be the ground of the finding (hereinafter, it may be referred to as an "attention site"), the physician correlates the medical image used for the determination of the finding (hereinafter, it may be referred to as a "key image") with the diagnostic report. The part to be the ground of the finding is a lesion site, such as a thrombus, a tumor, for example.

In addition, in order to clarify the attention site in the key image, the physician performs an operation for adding a shape, such as a circle and a polygon, called an annotation, to the key image.

In general, a wide range including an attention site is shown in a medical image. Therefore, when a key image to which an annotation is added is correlated with a diagnostic report as it is, it may be difficult for a doctor, and the like, who check the report to find each part shown in the medical image.

For that reason, the physician additionally generates an attention image showing the attention site, apart from the medical image obtained from the medical imaging apparatus. The physician also correlates the attention image, as well as the key image, with the diagnostic report. It is complicated for the physician to implement the work for generating the attention image and correlating the image with the diagnostic report for every interpretation. Further, it had been a problem that this work results deterioration of interpretation efficiency.

The present embodiments are intended to solve the above mentioned problem, and the object is to provide a report generation support apparatus and a report reading apparatus which are able to easily generate a diagnostic report.

BRIEF DESCRIPTION OF THE DRAWINGS

[FIG. 5] It is a flowchart illustrating an operation of the report generation apparatus according to the first embodiment.

DETAILED DESCRIPTION

In order to solve the above-described problem, the report generation support apparatus of the embodiments comprises a display, a specifying part, and a generator. The display configures to display a diagnostic report and a first medical image. The specifying part configures to specify a predetermined region or a predetermined position in the first medical image displayed on the display. The generator configures to generate a second medical image, based on the predetermined region or position specified by the specifying part, as well as the first medical image.

First Embodiment

Configurations of a report generation apparatus 4 according to the present embodiment are described with reference to FIG. 1 to FIG. 5.

Whole Configuration of Medical Information System 1

Figure 1:
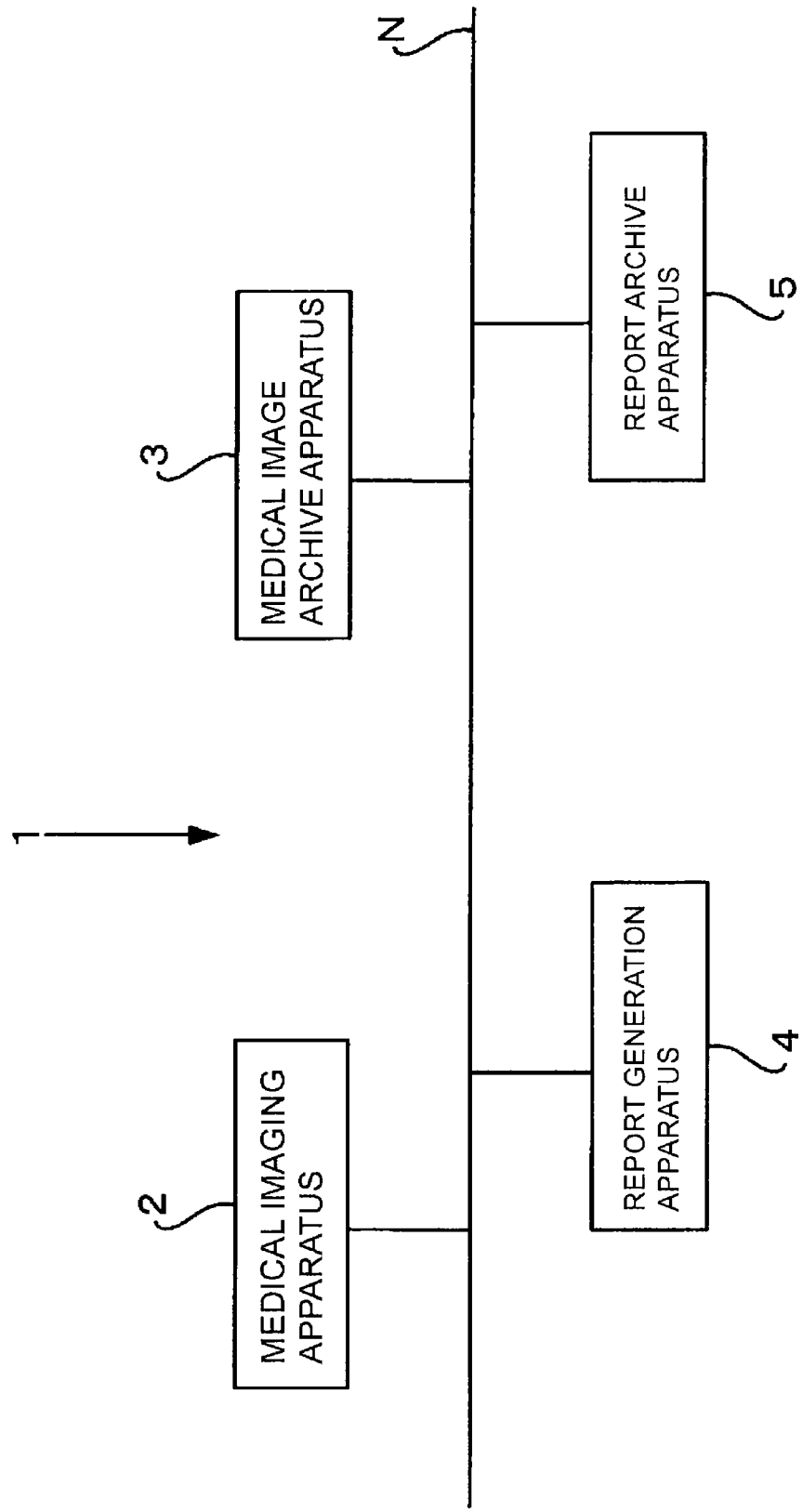
[FIG. 1] It is an overall view of a medical information system according to a first embodiment.

As shown in FIG. 1, a medical information system 1 comprises a medical imaging apparatus 2, a medical image archive apparatus 3, the report generation apparatus 4, and a report archive apparatus 5. These apparatuses are communicatably connected each other via a network N, such as LAN (Local Area Network). The communication between those apparatuses may conform to DICOM (Digital Imaging and Communications in Medicine) which is the medical image standard. Other standard rules, however, may be applied as the communication therebetween. TCP/IP (Transmission Control Protocol/Internet Protocol), for example, is used for the information communication. Also, data is transferred between those apparatuses by packet (basic unit for transferring information) communication via the network N.

The medical imaging apparatus 2 is, for example, an X-ray imaging apparatus, an X-ray CT (Computed Tomography) apparatus, a MRI (Magnetic Resonance Imaging) apparatus, or the like. The medical imaging apparatus 2 images a subject, and as a result, medical images may be obtained. The obtained medical images are sent to the medical mage archive apparatus 3, for example, in a file format which conforms to DICOM. The medical image to be send includes image correlation information accessory to the medical image, such as the date the image is obtained, imaging conditions, and the like. "Image" and "image data" correspond one to one, so that these may be treated as the same thing in the present embodiment.

The image archive apparatus 3 is an apparatus to archive the medical images sent from the medical imaging apparatus 2. The medical archive apparatus 3 is a so-called computer, and comprises inside a CPU (Central Processing Unit), ROM (Read Only Memory), RAM (Read Only Memory), and mass storing devices, and the like. The drawings of those CPU, ROM, RAM, and storing devices are omitted.

The report generation apparatus 4 records findings related to the medical image displayed on a display 43 (described later), based on an instruction from the physician, and the like. The report generation apparatus 4 also generates a diagnostic report. The detail description of the report generation apparatus 4 will be described later.

The report archive apparatus 5 archives the diagnostic reports generated by the report generation apparatus 4 and the medical images (key images) referred when the diagnostic reports are generated. The report archive apparatus 5 is a so-called computer, and comprises inside a CPU, ROM, RAM, mass storing devices, and the like. Drawings of those CPU, ROM, RAM, and mass storing devices are omitted. Further, the medical image archive apparatus 3 and the report archive apparatus 5 may be configured as a single apparatus. Otherwise, the report generation apparatus 4 and the report archive apparatus 5 may be configured as a single apparatus.

Configuration of Report Generation Apparatus

Figure 2:
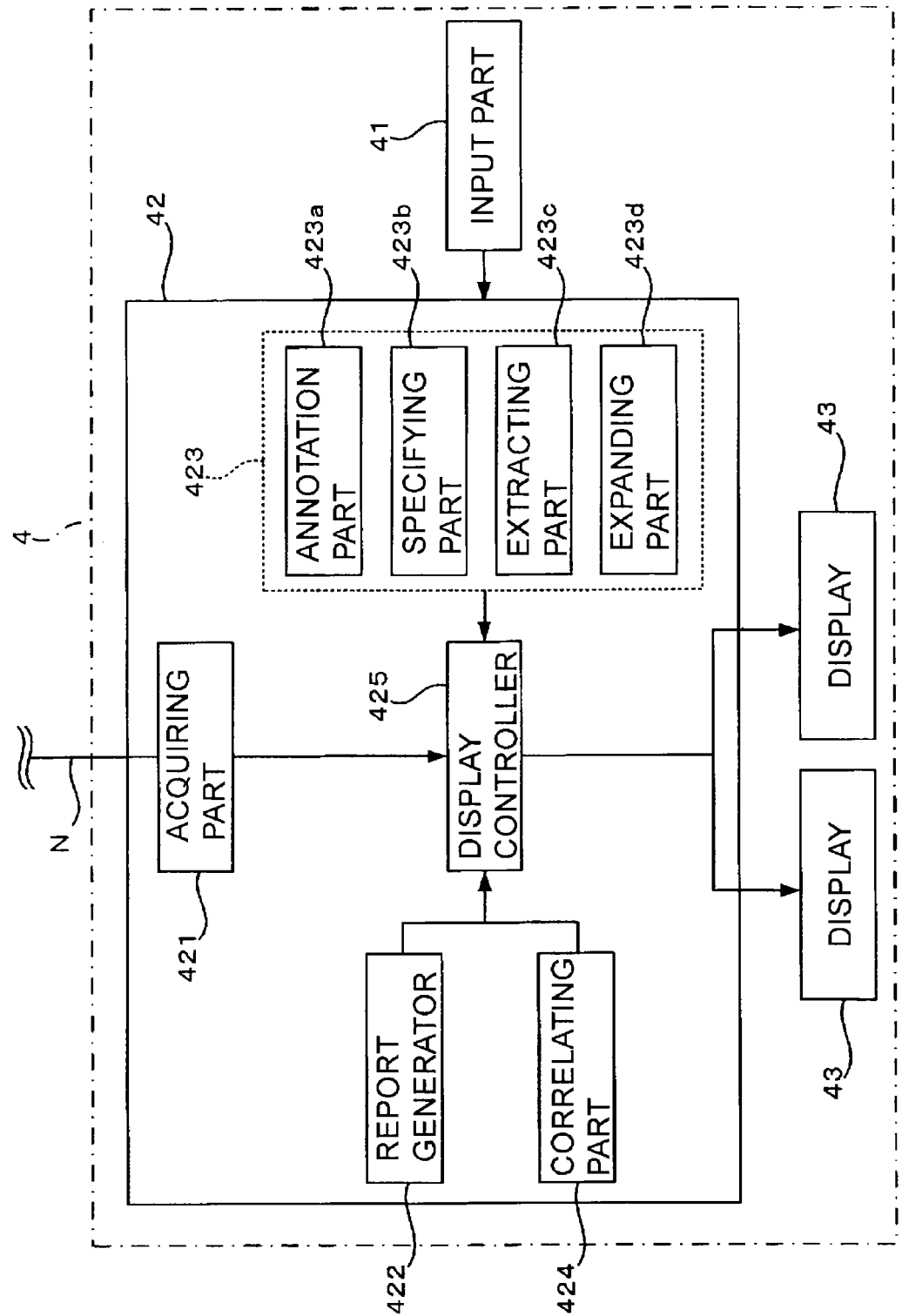
[FIG. 2] It is a diagram illustrating a report generation apparatus according to the first embodiment.

FIG. 2 is a block diagram illustrating the detail description of the report generation apparatus 4 according to the present embodiment. The report generation apparatus 4 comprises an input part 41, a CPU 42, and the display 43.

Input Device

The input part 41 in the report generation apparatus 4 is used to input various instructions. The input device 41 is, for example, a keyboard, a mouse, a trackball, a joystick, or the like. As the input part 41, GUI (Graphical User Interface) displayed on the display 43 may also be used. The input part 41 includes a pointing device which is able to designate at least any position within a medical image.

CPU

In the present embodiment, the CPU 42 functions as an acquiring part 421, a report generator 422, a processer 423, a correlating part 424, and a display controller 425.

Based on the instruction from the input part 41 or the like, the acquiring part 421 acquires medical images from the medical image archive apparatus 3. The medical images are referred when the physician and the like generate a diagnostic report. Specifically, when a test ID is input via the input part 41, the acquiring part 421 reads the medical images corresponding to the test ID from the medical image archive apparatus 3.

The report generator 422 causes content of findings to display in a finding input field displayed on the display 43, based on the instruction from the input part 41 or the like. Specifically, when the input part 41 is a keyboard, the report generator 422 records the character corresponding to the character key pressed by the physician, in the finding input field, as electric data. The report generator 422 then reflects the data of the recorded character to the finding input field.

The processor 423 implements various kinds of processing on the medical image obtained by the acquiring part 421. The processor 423 in the present embodiment comprises an annotation part 423*a*, a specifying part 423*b*, an extracting part 423*c*, and an expanding part 423*d*. The expanding part 423*d* corresponds to an example of a "generator".

The annotation part 423*a* adds annotations to the medical image displayed on the display 43, based on the instruction from the input part 41 or the like. An annotation is, for example, a shape, such as an arrow pointing an attention site (lesion site, and the like), a circle, an ellipse, and a polygon surrounding the attention site, and a line drawn by freehand, delineated on the medical image. Specifically, the physician selects an annotation of a circle shape, and instructs to surround the attention site in the medical image using the input part 41, such as a mouse. According to the input, the annotation part 423*a* causes an annotation A of the circle shape to be displayed on the target part in the medical image (see FIG. 3A). A plural number of annotations may be added to a single medical image.

The specifying part 423*b* specifies an image region in the medical image displayed on the display 43. Any well-known methods may be used to specify the image region. A specific example is described with reference to FIG. 3A. The specifying part 423b detects a circumference (perimeter) of the annotation A by implementing edge detection processing or the like for the medical image to which the annotation A has been added. The specifying part 423b also specifies the circumference and a part (plane) within the circumference, as an image region. When annotations are added to more than one part in a single medical image, and when an annotation is added to each of a plurality of medical images, the specifying part 423b implements the above mentioned processing to each of the annotations on each of the medical images. The processing by the specifying part 423b may be started by the instruction from the input part 41 or the like. Otherwise, the processing may be started automatically in accordance with detection by the specifying part 423b, the detection being the detecting the addition of the annotation to the medical image.

The image region is not limited to the plane mentioned in the specific example. For example, the image region may be any of a point, a line, and a solid. That is, the image region may be any of zero-dimensional (point) to three-dimensional (solid) shapes. For other specific example, in the medical image to which an arrow annotation A' is added shown in FIG. 4A, the specifying part 423b may specify a part indicating the tip-end of the arrow (point P; see in FIG. 4B), as the image region.

Also, the image region specified by the specifying part 423b dose not have to include the all of the annotations. For example, when some of the annotations are designated by the physician and the like through the input part 41, the specifying part 423b may specify the designated range as the image region. The image region described above corresponds to an example of a "predetermined region" or a "predetermined position".

The extracting part 423c extracts an image of a predetermined range including the image region specified by the specifying part 423b. As a specific example, in the medical image to which the annotation A of the circle shape is added (see FIG. 3A), a case that the circumference of the annotation and a part within the circumference are specified as the image region is described. Firstly, the extracting part 423c determines a rectangle R (quadrangle in the embodiment) circumscribing to the specified image region (see FIG. 3B). The extracting part 423c then determines the range expanded by a predetermined length evenly from each vertex of the rectangle R, as a predetermined range PR (see FIG. 3C). Lastly, the extracting part 423c extracts the image of the predetermined range PR by trimming (see FIG. 3D). The range expanded from the predetermined range PR or the rectangle R may be set with a predetermined value in advance. Otherwise, those ranges may be arbitrarily set every time in accordance with the image region specified by the specifying part 423b. Further, the range expanded from the rectangle R may not be evenly expanded from each vertex of the rectangle R. When a plurality of image regions is specified, the extracting part 423c implements the above mentioned processing to each of the specified image regions.

Furthermore, the extracting part 423c may cause the display 43 to display the predetermined range PR. This processing makes it possible for the report generation apparatus 4 to present the range to extract to the physician and the like. As a result, the physician and the like are able to understand the range to be extracted. In addition, the display screen for the predetermined range PR may be configured such that the physician and the like can perform edit operation thereto via the input part 41 or the like. When the operation is applied, the extracting part 423c changes the predetermined range PR displayed on the display 43. In this case, the extracting part 423c implements extraction processing on the predetermined region PR after the change.

Even when a polygon or a shape drawn by freehand are added, the same processing as above may be processed. That is, the extracting part 423c determines a rectangle circumscribing to the polygon or the shape drawn by freehand specified by the specifying part 423b. The extracting part 423c then determines the range expanded evenly from each vertex of the rectangle as a predetermined range. Lastly, the extracting part 423c extracts the image of the predetermined range by trimming.

As another specific example, in the medical image to which the arrow annotation A' pointing the attention site is added (see FIG. 4A), a case that the tip-end (point P) of the arrow is specified as the image region (see FIG. 4B) is described. The extracting part 423c determines the range, including the specified point P (image region), expanded evenly from the point P in the predetermined directions, as a predetermined range PR' (see FIG. 4C). The extracting part 423c then extracts the image of the predetermined region PR' by trimming (see FIG. 4D).

Figure 3A:
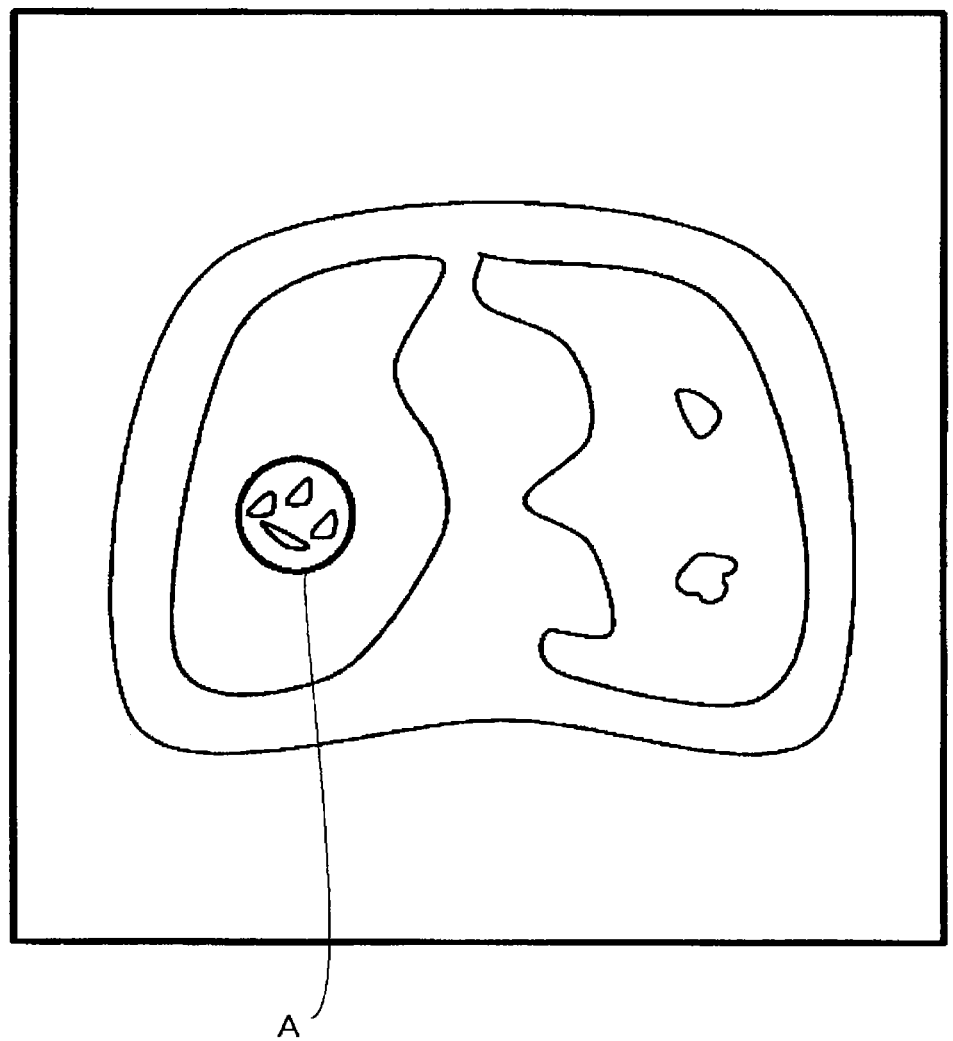
[FIG. 3A] It is a diagram illustrating an example of medical images according to the first embodiment.

The expanding part 423d generates an expanded image corresponding to the image extracted by the extracting part 423c. The generated expanded image is displayed on the display 43. The expanded image may be generated based on either the medical image used to add the annotation, or the extracted image. For example, when the expanded image is generated based on the medical image, the expanding part 423d implements processing to expand the region corresponding to the predetermined range PR in the medical image. It is possible to degradation in image quality of the expanded image by generating the expanded image from the medial image. In addition, when the image extracted by the extracting part 423c (see FIG. 3D) is expanded, the expanding part 423d expands the image at a predetermined magnification (see FIG. 3E) by using an interpolation method which interpolates an estimated pixel between pixels forming the image, or the like. In FIG. 3E, the image is expanded to the same size as the original medical image (FIG. 3A). As the magnification, a predetermined rate may be set in advance, or a rate may be set every time by an operator. When images of a plurality of parts in the medical image are extracted, the expanding part 423d implements the above described processing on each extracted image (see FIG. 4E).

The correlating part 424 correlates the expanded image generated by the expanding part 423d with a diagnostic report after receiving the instruction via the input part 41. A specific example of the correlation processing is described with reference to FIG. 3F and FIG. 3G. FIG. 3F is a schematic diagram schematically illustrating an operation to correlate an expanded image M1 with a diagnostic report RA. FIG. 3G is a schematic diagram schematically illustrating a process to correlate the expanded image M1 with the diagnostic report RA.

As shown in FIG. 3F, when the operator drags and drops the expanded image M1 displayed on the display 43 and then drops onto any of regions within the diagnostic report RA by using the input part 41, such as a mouse, the correlating part 424 receives an instruction in accordance with the operation. Also, as shown in FIG. 3G, the correlating part 424 correlates, according to the instruction, the expanded image M1 with an arbitrary part in the diagnostic report RA. The expanded image corresponds to an example of a "second image". Further, the original medical image of the expanded image corresponds to an example of a "first medical image".

Correlation Example 1

An example of processing for "correlating an image with a diagnostic report" described above may be explained as processing which pastes image data to diagnostic report data. For example, the correlating part 424 converts a DICOM image into a general-purpose file format, such as JPEG. The correlating part 424 then implements processing for embedding the converted image to the diagnostic report data. In a case that a test requesting doctor brows the diagnostic report using a PC, the diagnostic report and the image data of the embedded expanded image are read out. As a result, both the diagnostic report and the expanded image are displayed on the display of the PC or the like.

Correlation Example 2

The correlation processing by the correlating part 424 also includes processing such that the correlating part 424 correlates the expanded image with the diagnostic report and stores in a storing device or the like. For example, the medical information system 1 may be configured such that the expanded image is correlated with the original medical image and stored in the medical mage archive apparatus 3. In this configuration, the correlating part 424 correlates the image data of the expanded image with an image ID of the image data of the original medical image, or an ID (report ID, patient ID, or the like) for identifying storage positional information of the image data of the original medical image, the diagnostic report, to store in the medical mage archive apparatus 3. Further, the correlating part 424 implements processing for embedding image data link information of the expanded image to the diagnostic report data. When the test requesting doctor brows the diagnostic report, the diagnostic report as well as the image data link information of the expanded image are read out from the doctor's PC. In accordance with the link information, the image data is read out. Through those respective processes, the diagnostic report and the expanded image are displayed on the display of the PC or the like. The image data of the expanded image may be a DICOM image, or general-purpose image data, such as JPEG.

Correlation Example 3

The correlation processing by the correlating part 424 also includes processing such that the correlating part 424 correlates image processing conditions when the expanded image is generated with the diagnostic report, to store in a storing device or the like. For example, the medical information system 1 may be configured such that the image processing conditions of the expanded image is correlated with the original medical image and stored in the medical mage archive apparatus 3. In this configuration, the correlating part 424 obtains the image processing conditions of the expanded image from the expanding part 423*d* or the like. The image processing conditions include, in the original medical image, positional information (coordinate information), resolution, magnification, conditions for the interpolation, and the like.

The correlating part 424 also correlates the image processing conditions with the image ID or the storing positional information of the image data of the original medical image, or the ID (report ID, patient ID, or the like) for identifying the storing positional information or the diagnostic report, to store in the medical mage archive apparatus 3. Further, the correlating part 424 implements processing for embedding link information of the image processing conditions to the diagnostic report data. When the test requesting doctor brows the diagnostic report, the diagnostic report as well as the image data of the original medical image correlated with the diagnostic report and the embedded link information of the image processing conditions of the expanded image are read out from the doctor's PC. In accordance with the link information, the image processing conditions are read out. The test requesting doctor's PC implements image processing for the image data of the original medical image, based on the read out image processing conditions. As a result, the PC generates image data of the expanded image. Through those respective processes, the diagnostic report and the expanded image are displayed on the display of the PC or the like. The image data of the expanded image is a DICOM image or the like.

The correlating part 424 may also implements processing such as correlating the diagnostic report with expanded image position (displaying position) information, expanded image size information, as well as a display mode for the expanded image or the medial image therein.

Figure 3B:
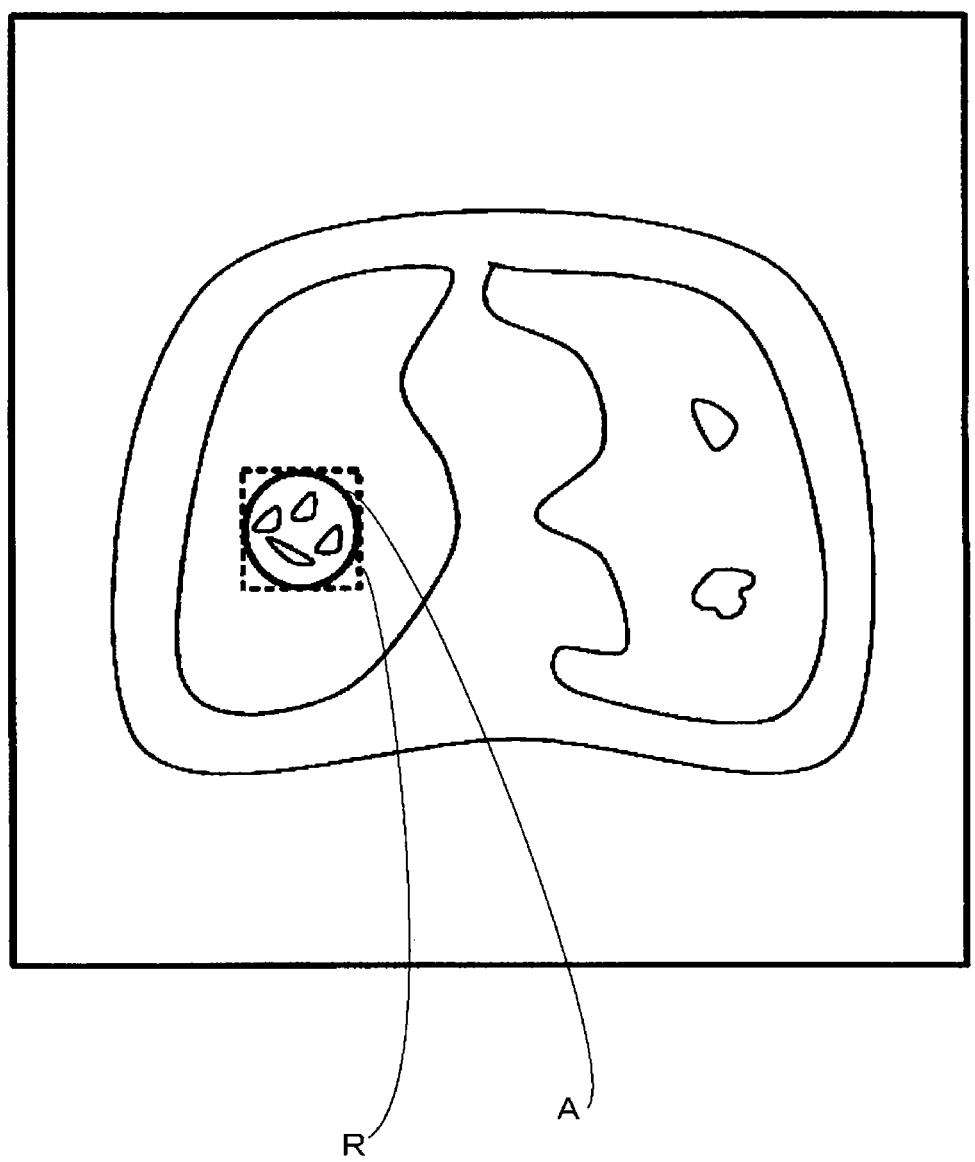
[FIG. 3B] It is a diagram illustrating an example of the medical images according to the first embodiment.
Figure 3C:
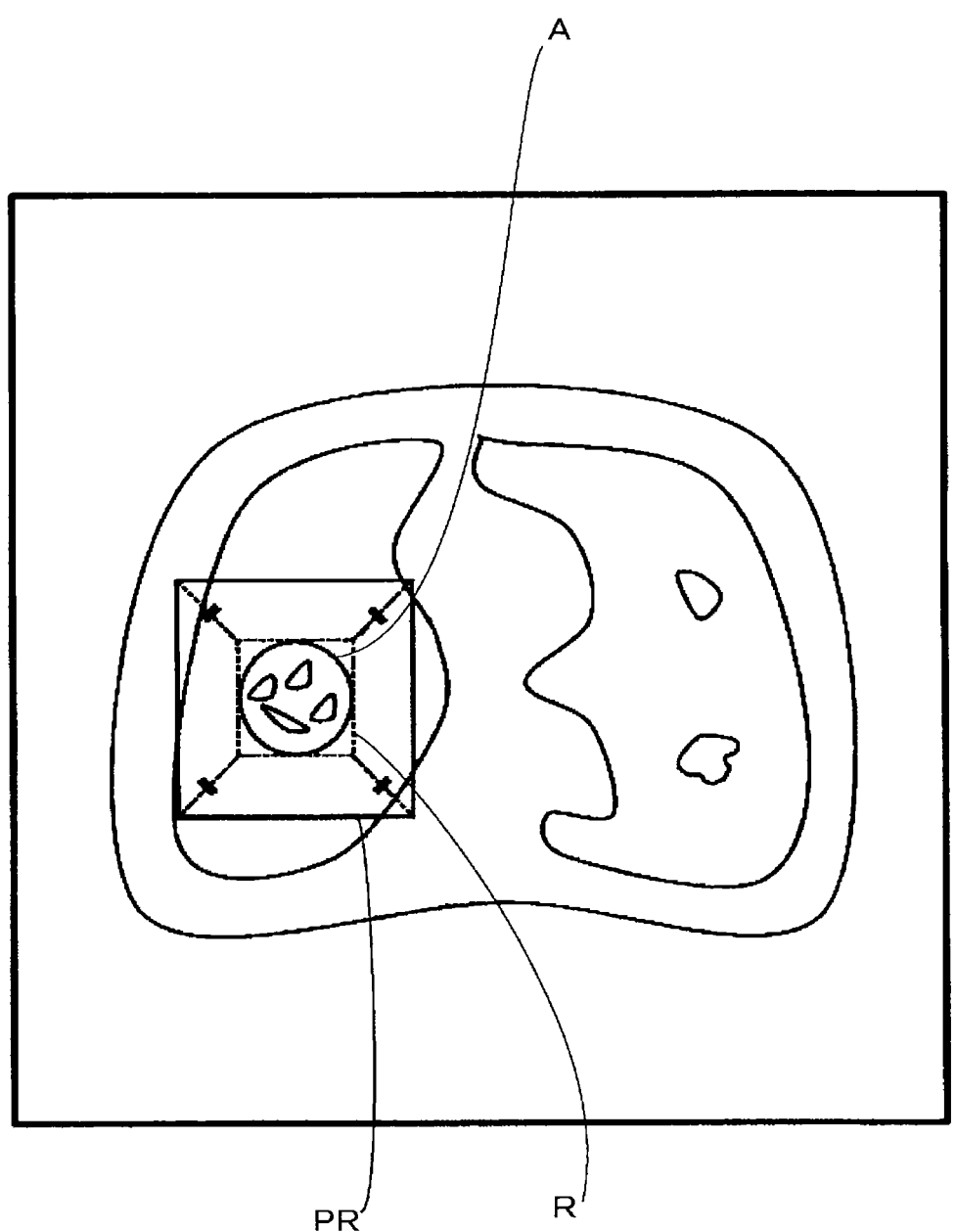
[FIG. 3C] It is a diagram illustrating an example of the medical images according to the first embodiment.
Figure 3D:
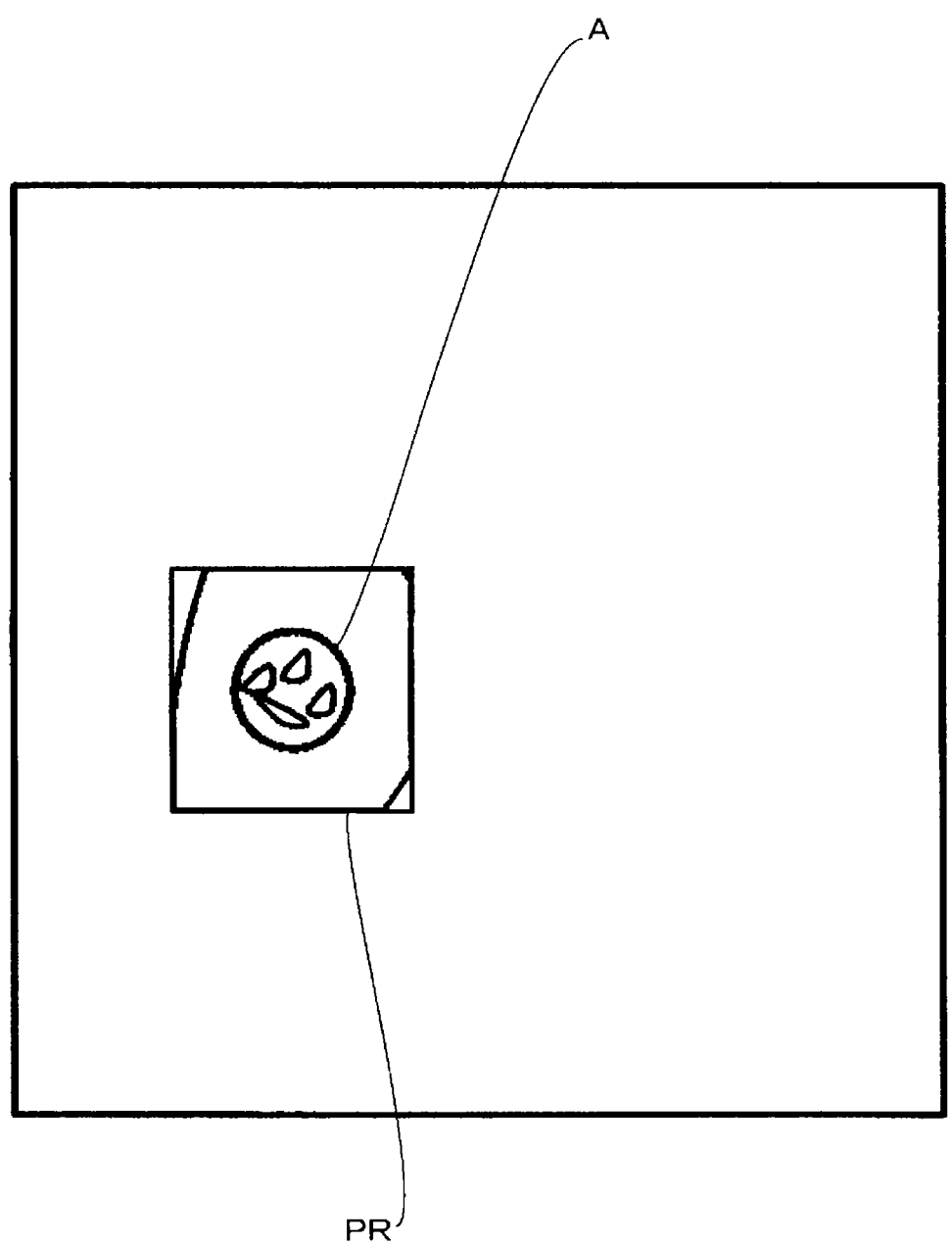
[FIG. 3D] It is a diagram illustrating an example of the medical images according to the first embodiment.
Figure 3E:
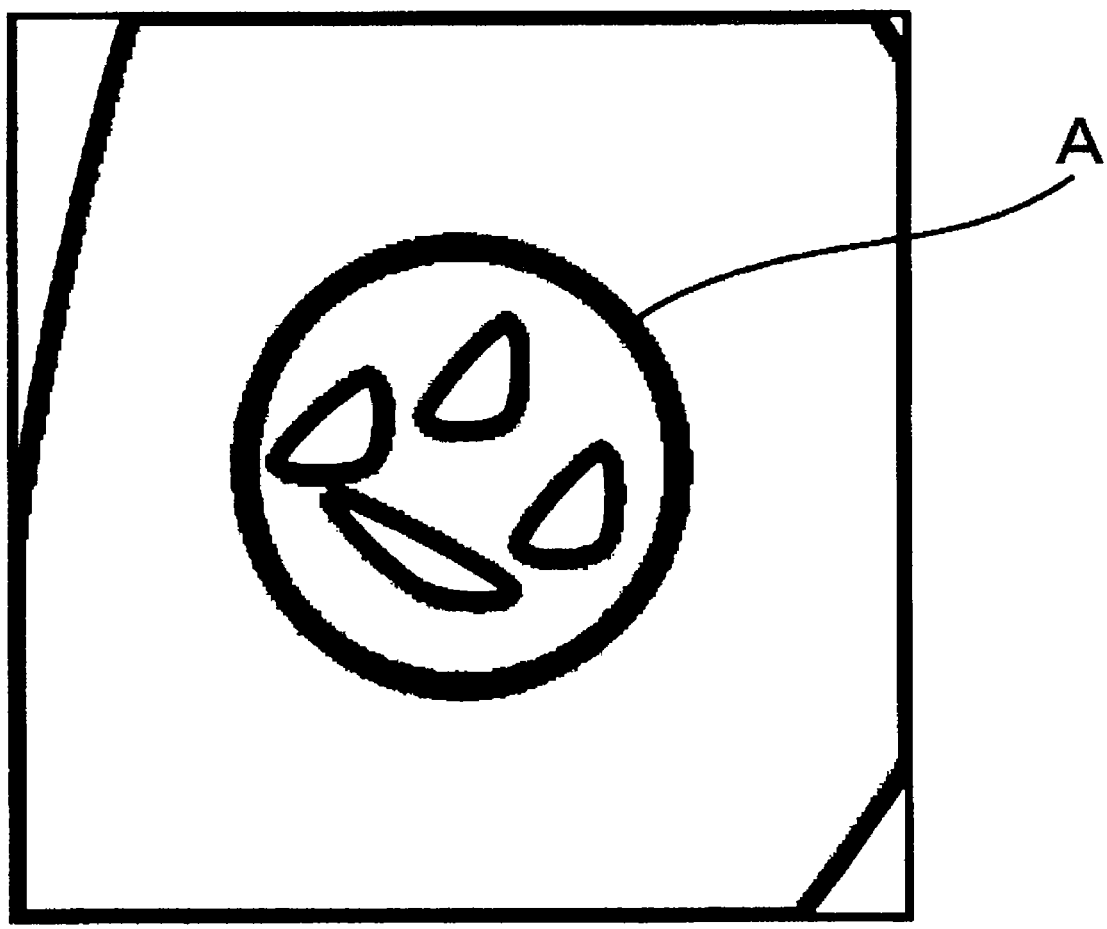
[FIG. 3E] It is a diagram illustrating an example of the medical images according to the first embodiment.
Figure 3F:
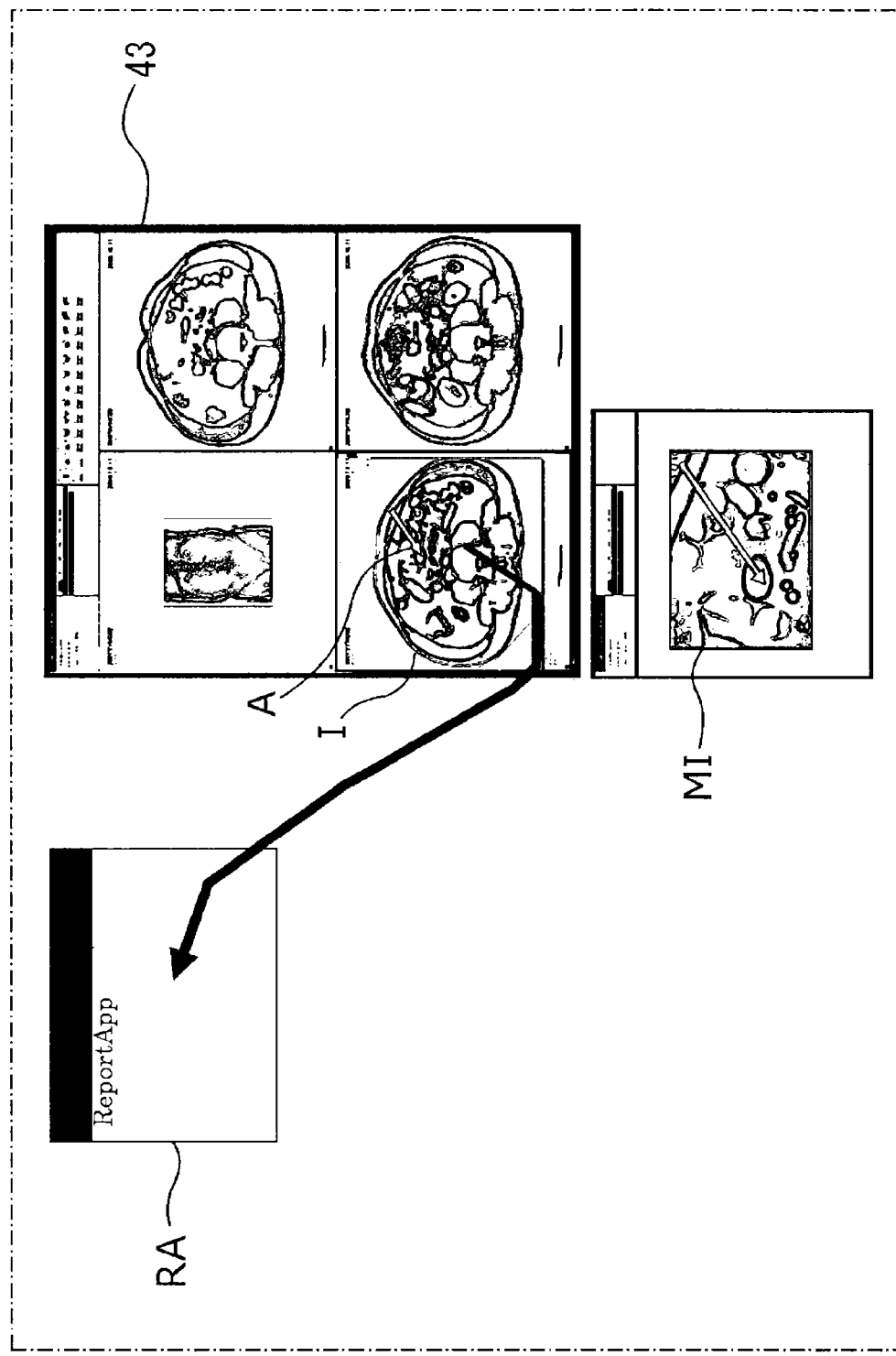
[FIG. 3F] It is a schematic diagram schematically illustrating an operation for correlating an expanded image with a diagnostic report.
Figure 3G:
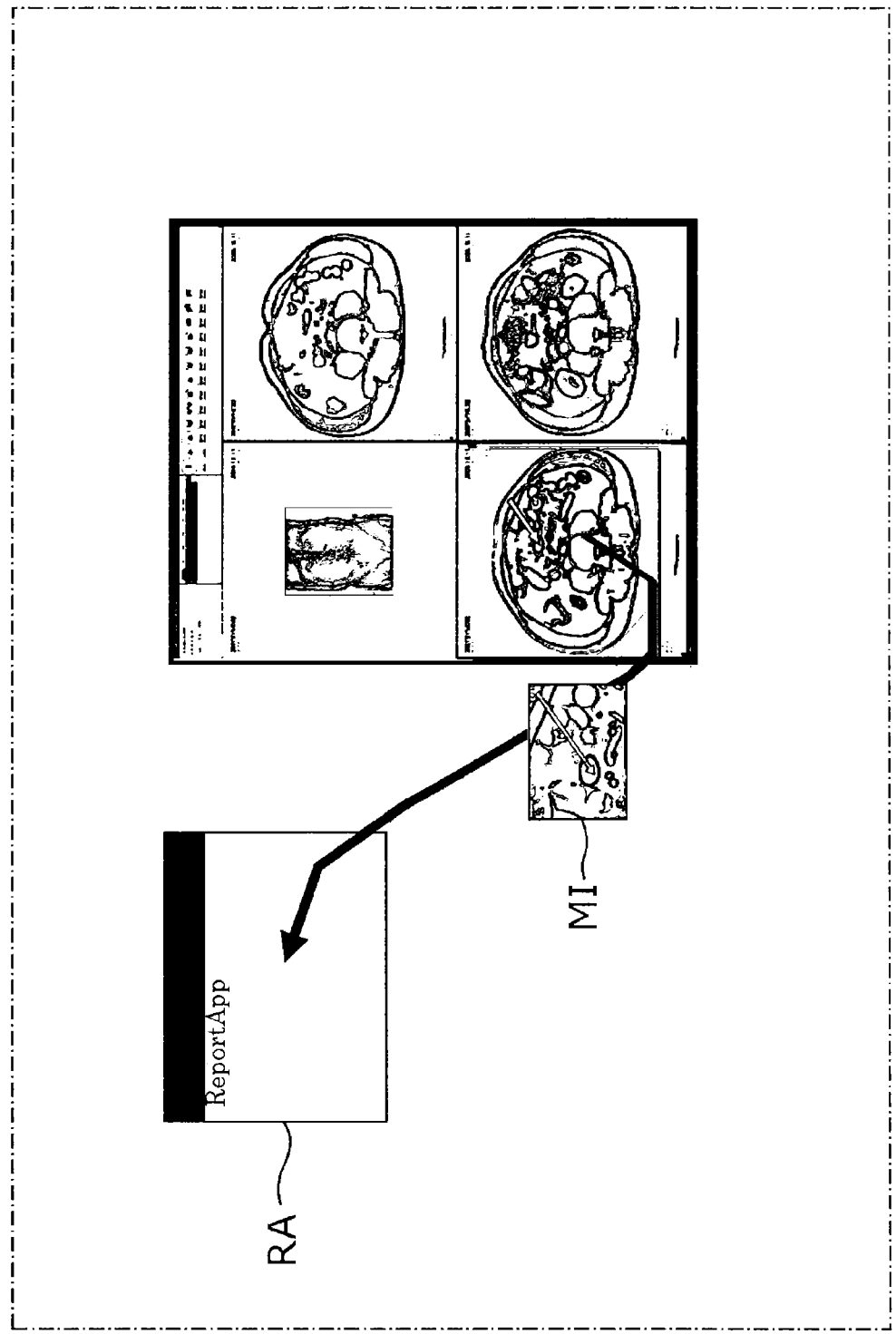
[FIG. 3G] It is a schematic diagram schematically illustrating a process for correlating the expanded image with the diagnostic report.
Figure 3H:
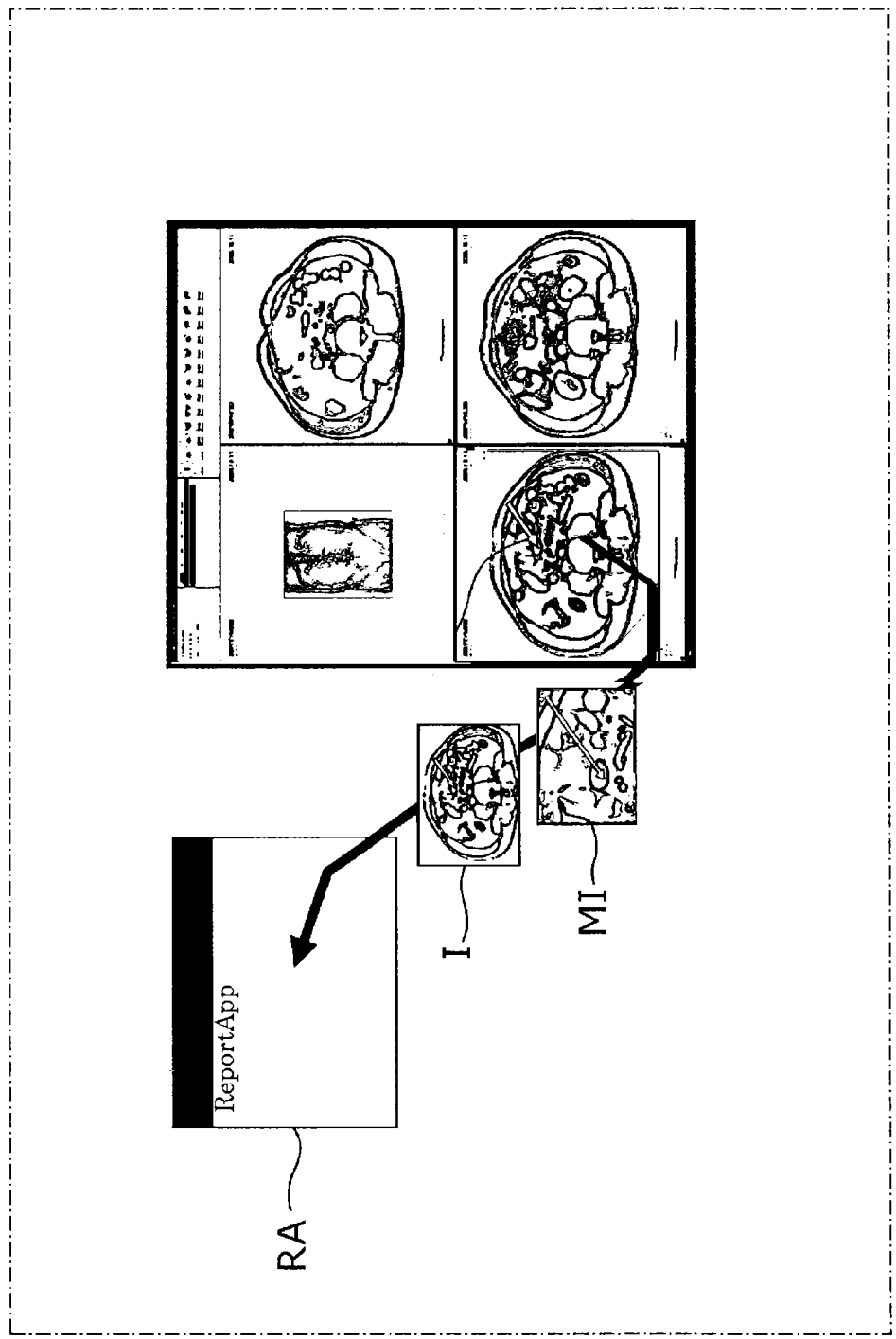
[FIG. 3H] It is a schematic diagram schematically illustrating another process for correlating the expanded image with the diagnostic report.

As shown in FIG. 3H, it is also possible for the correlating part 424 to correlate the expanded image M1 as well as a medical image I which is a source of the expanded image M1 with the diagnostic report RA. It is also possible for the correlating part 424 to correlate the other medical images or the like displayed on the display 43 with the diagnostic report. Alternatively, when a plurality of expanded images is displayed on the display 43, it is possible for the correlating part 424 to correlate each of the expanded images with a single diagnostic report, in accordance with the operation. The display mode for the images after reading out from the test requesting doctor's PC or the like will be described later.

The display controller 425 implements display control for the display 43. For example, the display controller 425 controls so as to cause the display 43 to display the medical image obtained by the acquiring part 421, the diagnostic report, and the like (see FIG. 4E).

Display

The display 43 is a display to display diagnostic reports and medical images. In the present embodiment, a dual display having two of the display 43 is used. The diagnostic reports are displayed on one side of the displays 43, and the medical images are displayed on the other side thereof. When there is a plurality of medical images obtained by the acquiring part 421, the display 43 may be caused to display all of the medical images.

In the present embodiment, among the above configuration, the specifying part 423*b*, the correlating part 424, and the display 43 are an example of a "report generation support apparatus". The input part 41, the extracting part 423*c*, and the expanding part 423*d* may also be included as the example of the "report generation support apparatus".

Operation

Next, operations of the report generation apparatus 4 according to the present embodiment are described with reference to FIG. 5.

Firstly, the report generation apparatus 4 is activated by the operator. The display controller 425 causes the display 43 to display a diagnostic report generation screen including the finding input field (S10), after the report generation apparatus 4 is activated.

Next, in accordance with the input of the test ID through the input part 41 by the operator, the acquiring part 421 acquires the medical image related to the test ID from the medical image archive apparatus 3. The display controller 425 causes the display 43 to display the medical image acquired (S11).

The physician observes the medical image displayed on the display 43, and finds findings. The physician then implements an operation to input the findings to the diagnostic report generation screen displayed on the display 43 via the input part 41. At this time, the physician may implement an operation to add annotations, using the input part 41, to any part within the medical image referred at the time of generating the diagnostic report. Based on the operation, the annotation part 423a adds annotations to the medical image (S12). Hereinafter, in S12, the case when the operation in which the circle annotation A is added by the physician is implemented is described (see FIG. 3A).

When the annotation A is added, the specifying part 423b detects the circumference of the circle annotation A by the edge detection. The specifying part 423b further specifies the circumference and the part within the circumference as the image region (S13).

The extracting part 423c determines the rectangle R (quadrangle) circumscribing to the specified image region (see FIG. 3B). The extracting part 423c then determines the predetermined range PR expanded by a predetermined length evenly from each vertex of the rectangle R (see FIG. 3C). The extracting part 423c further extracts the image of the predetermined range PR by trimming (S14; see FIG. 3D).

The expanding part 423d generates an expanded image corresponding to the image extracted in S14 (S15; see FIG. 3E). There is a case that a plurality of annotations is added. That is, for example, there is a case when a plurality of annotations is added to a single medical image or a case when an annotation is added to each of a plurality of medical images. In any case, the report generation apparatus 4 implements processing from S13 to S15 for each of the annotations.

The display controller 425 causes the display 43 to display the expanded image generated in S15 (S16).

The physician instructs, via the input part 41, to correlate the expanded image displayed in S16 with the diagnostic report (see FIG. 3F). Based on the instruction, the correlating part 424 correlates the expanded image generated in S15 with the diagnostic report (S17) (see FIG. 3G). The diagnostic report correlated with the medical image is generated based on these processes (S18).

Expanded Image Acquiring Processing

The diagnostic report correlated with the expanded image is stored, for example, with the report ID and the like, in a storage storing diagnostic reports. When a request to read out the report is made via a terminal connected to the report storage, the diagnostic report corresponding to the request is send to the terminal. In the example shown in FIG. 1, the diagnostic report is stored in the report archive apparatus 5 in the medical information system 1. Hereinafter, based on the medical information system 1 shown in FIG. 1, display modes for the diagnostic report are described.

The test requesting doctor and the like, for example, input an arbitrarily report ID and the like, and make a diagnostic report acquisition request via a PC terminal connected to the medical information system 1 and the like. The report archive apparatus 5 receives the acquisition request and the report ID, and sends the diagnostic report corresponding to the report ID to the PC terminal. The PC terminal which is used to make the request receives the diagnostic report data.

Here, the PC terminal causes a display (not shown) to display the diagnostic report and the expanded image correlated therewith, based on the information embedded to the diagnostic report.

As a first example, when the image data of the expanded image is embedded to the diagnostic report, the PC terminal causes the display to display the expanded image to be displayed, based on the embedded image data. As a second example, when the link information of the expanded image is embedded to the diagnostic report, the PC terminal acquires the image data corresponding to the link information from the medical image archive apparatus 3, based on the link information of the embedded image. The PC terminal further causes the expanded image corresponding to the image data as well as the diagnostic report to be displayed.

As a third example, when the link information of the medical image which is the source of an expanded image and the image processing conditions for the expanded image are embedded to the diagnostic report, the PC terminal acquires the image data corresponding to the link information from the medical image archive apparatus 3, based on the link information of the embedded image. Further, the PC terminal implements the embedded image processing conditions to the medical image corresponding to the image data to generate the expanded image. The PC terminal then causes the diagnostic report and the generated expanded image to be displayed.

As a forth example, when the link information of the medical image which is the source of an expanded image and the link information of image processing conditions for the expanded image are embedded to the diagnostic report, the PC terminal acquires the image data corresponding to the link information from the medical image archive apparatus 3, based on the link information of the embedded image. Further, the PC terminal acquires the image processing conditions based on the link information of the image processing conditions for the expanded image from any of storing apparatuses in the medial information system 1. The PC terminal then applies the acquired image processing conditions to the medical image corresponding to the image data to generate the expanded image. Further, the PC terminal causes the diagnostic report and the generated expanded image to be displayed. In this example, the image data for the medical image may be embedded to the diagnostic report.

In the above described first example to fourth example, the PC terminal may be caused to acquire the medical image which is the source of the expanded image. Also, as an embodiment in which the PC terminal acquires the expanded image, the above described examples are not limited thereto. Further, the expanded image correlated with the diagnostic report may be corresponded to the information of the diagnostic report arranging position in the image display field and the information related to display modes for the source medical image.

Display Modes

Next, display modes when the diagnostic report and the expanded image which is generated according to the above embodiment and correlated with the diagnostic report are displayed are described with reference to FIG. 4E to FIG. 4L. From FIG. 4F to FIG. 4I are schematic diagrams each illustrating an outline of the medial image and the expanded image displayed with the diagnostic report. FIG. 4F to FIG. 4L each displays the expanded image or medical image in different display modes from each other. Each of these display modes are displayed in accordance with the information related to the display of the image correlated with the diagnostic report.

As described above, the diagnostic report may be correlated with the information related to the arranging position and the display mode for the expanded image and the arranging position and the display mode for the source medical image, in the image display field in the diagnostic report. Based on the correlated information, the PC terminal causes the display or the like to display the expanded image and the source medical image, for example, in the following display modes.

First Example

Figure 4A:
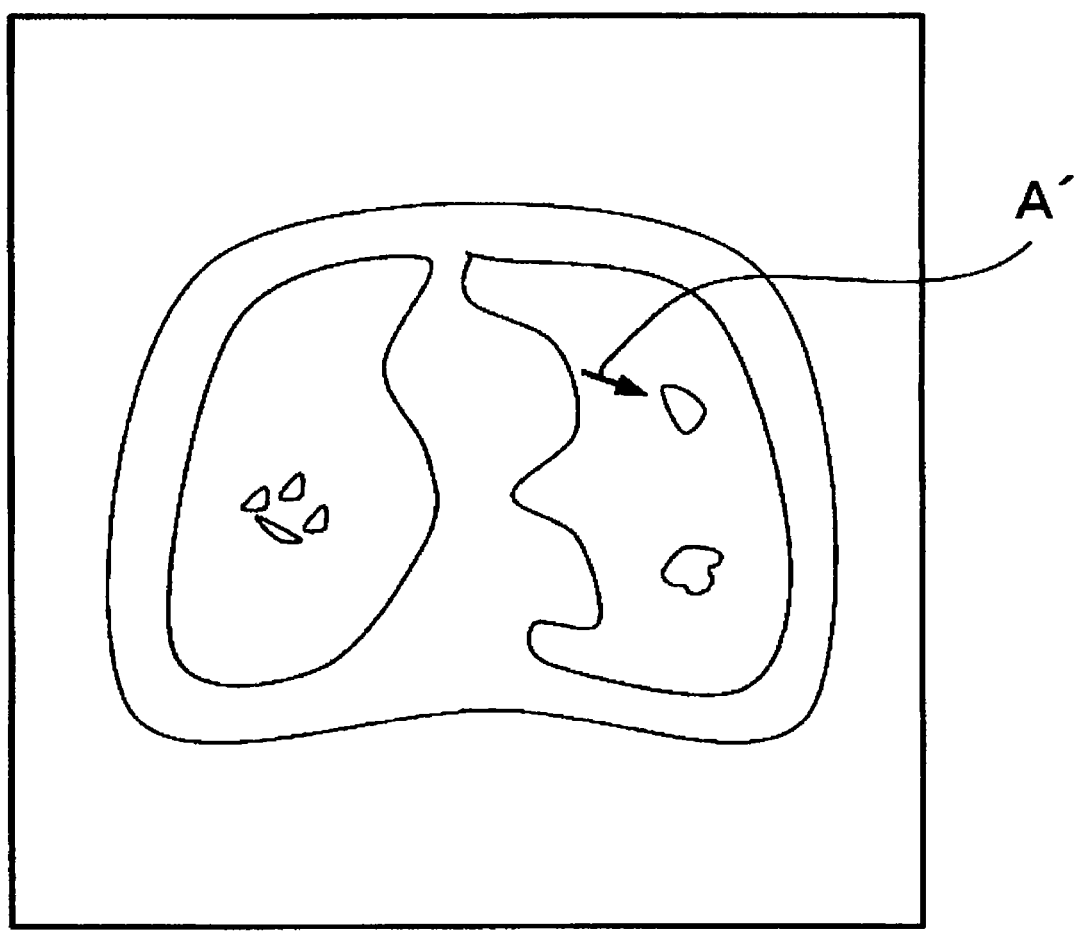
[FIG. 4A] It is a diagram illustrating another example of the medical images according to the first embodiment.
Figure 4B:
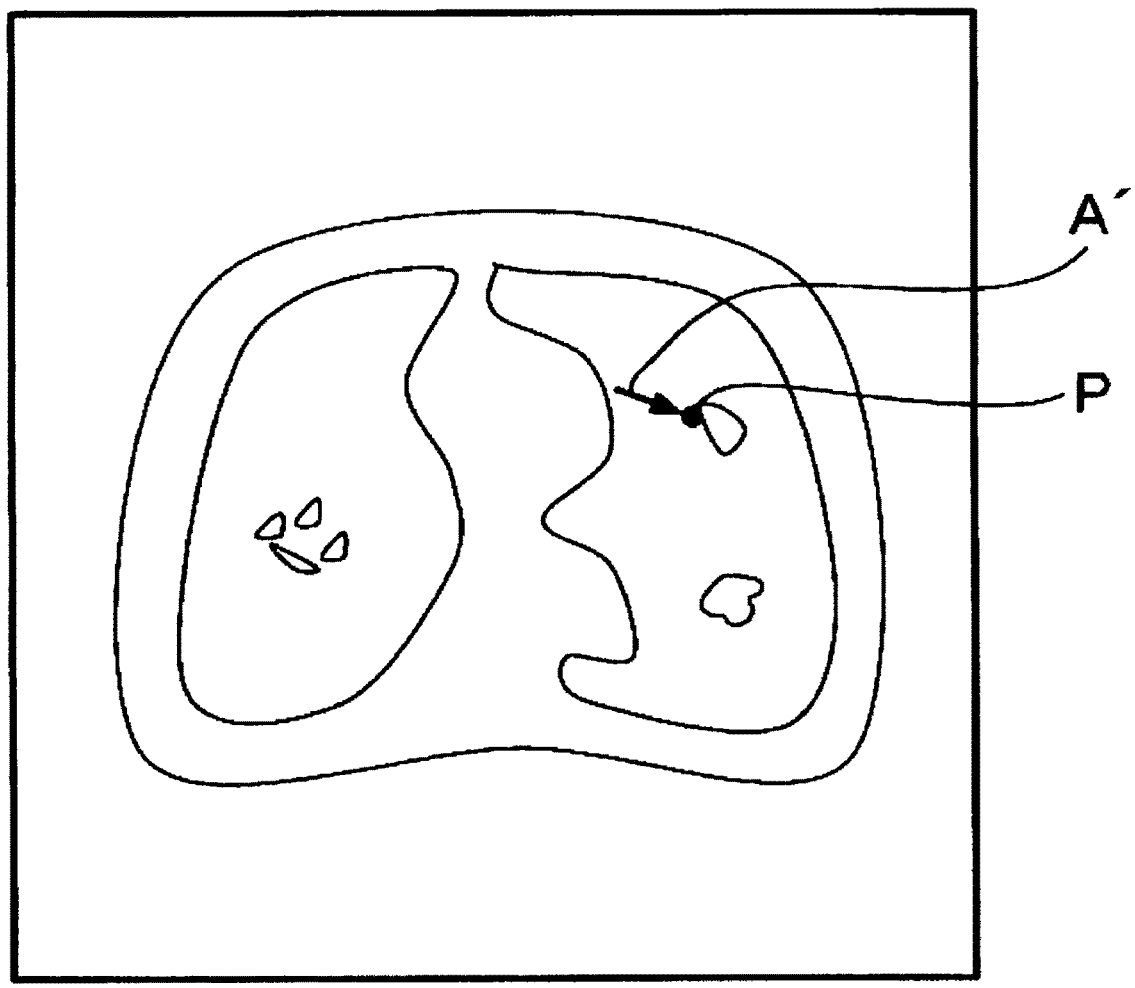
[FIG. 4B] It is a diagram illustrating another example of the medical images according to the first embodiment.
Figure 4C:
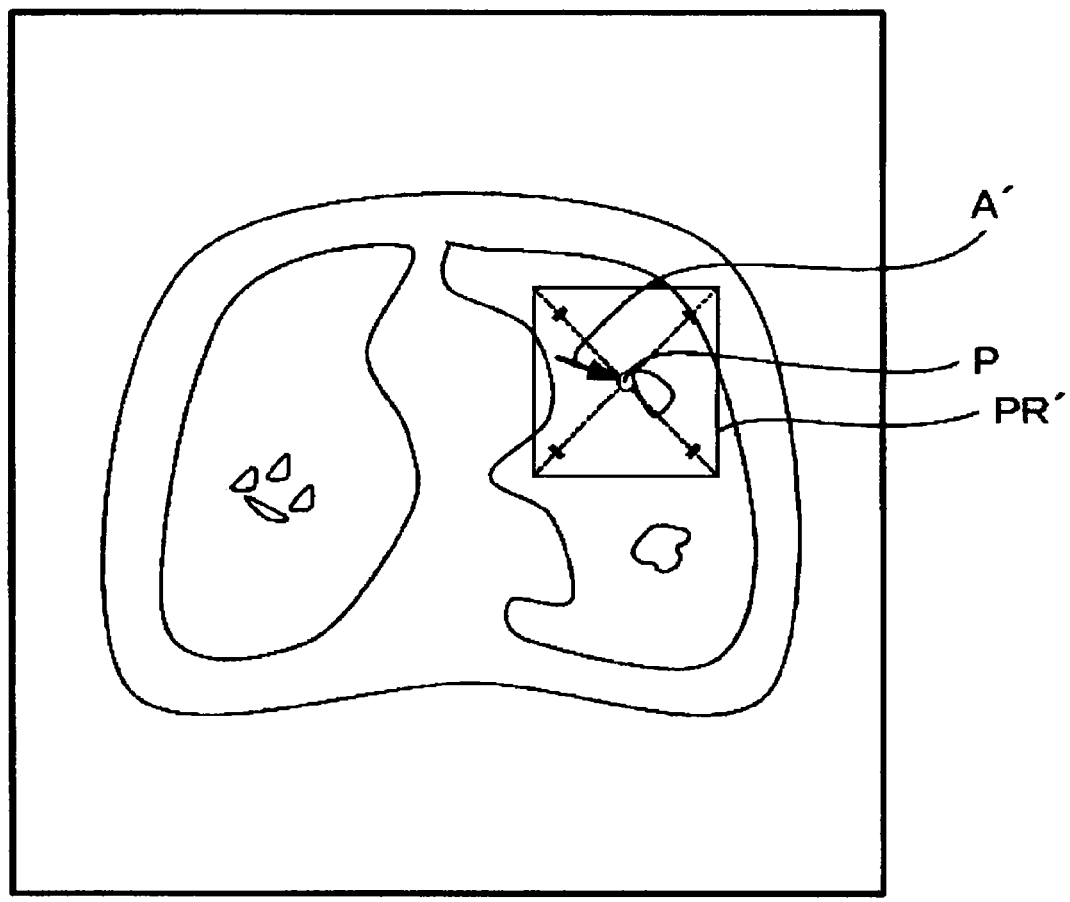
[FIG. 4C] It is a diagram illustrating another example of the medical images according to the first embodiment.
Figure 4D:
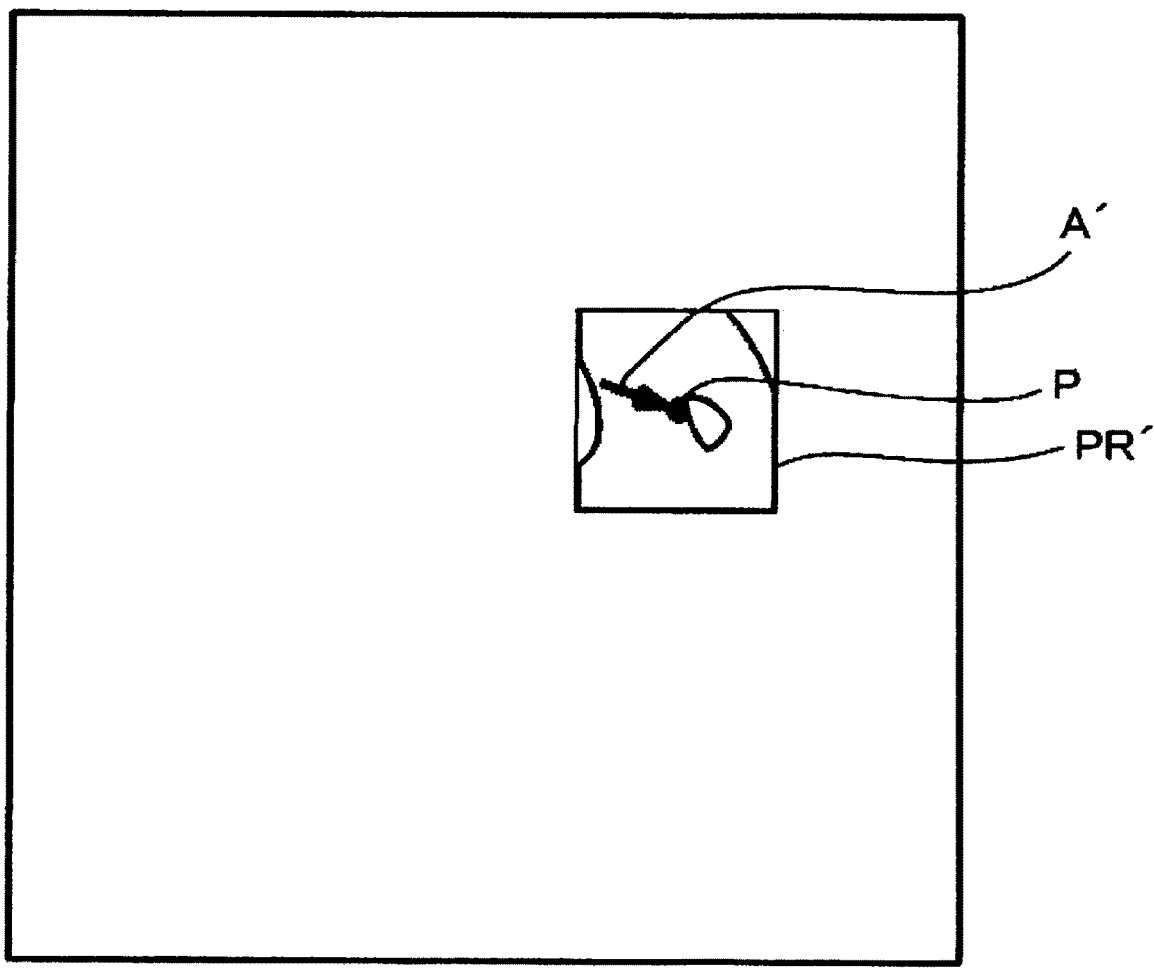
[FIG. 4D] It is a diagram illustrating another example of the medical images according to the first embodiment.
Figure 4E:
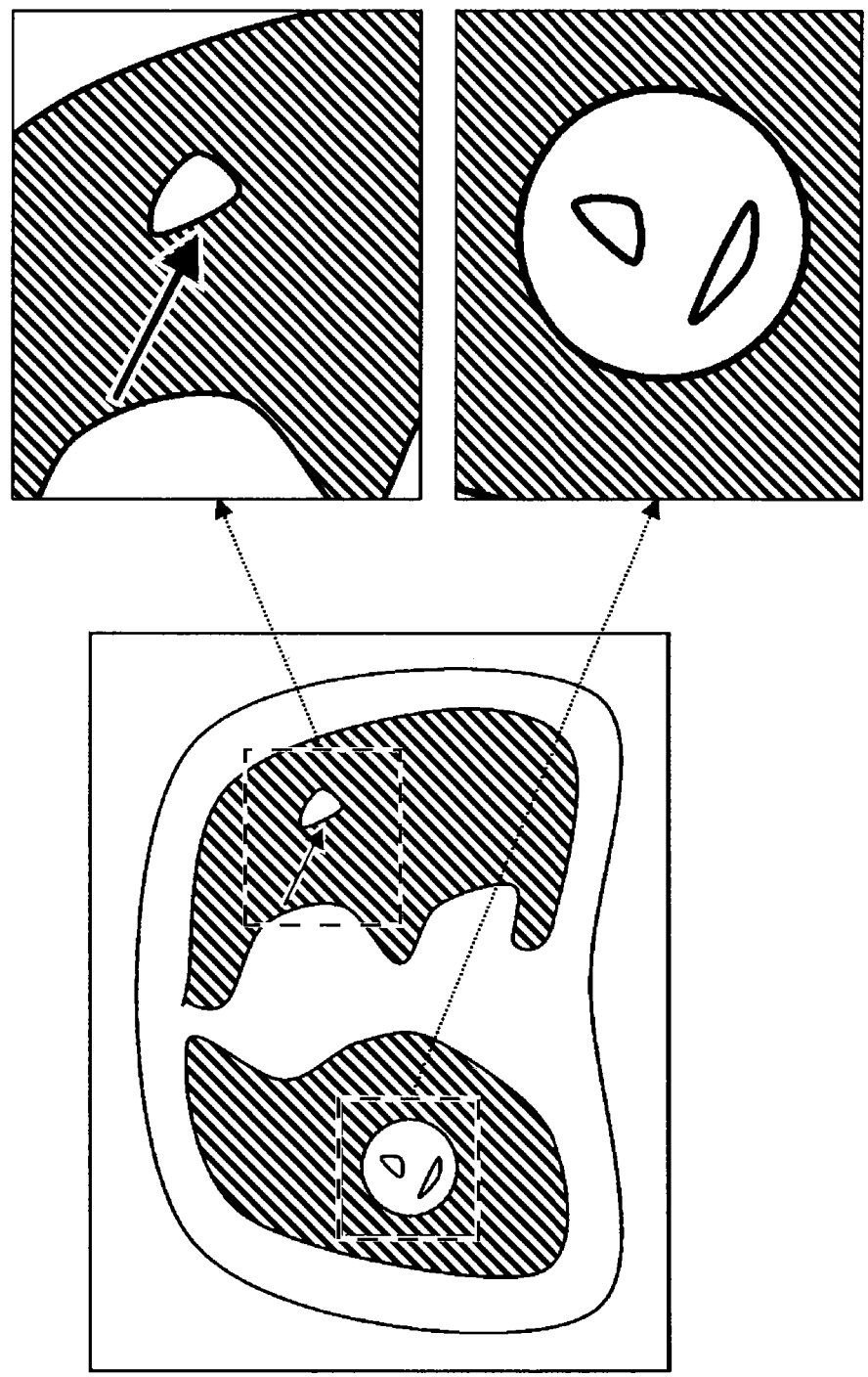
[FIG. 4E] It is a diagram illustrating another example of the medical images according to the first embodiment.
Figure 4F:
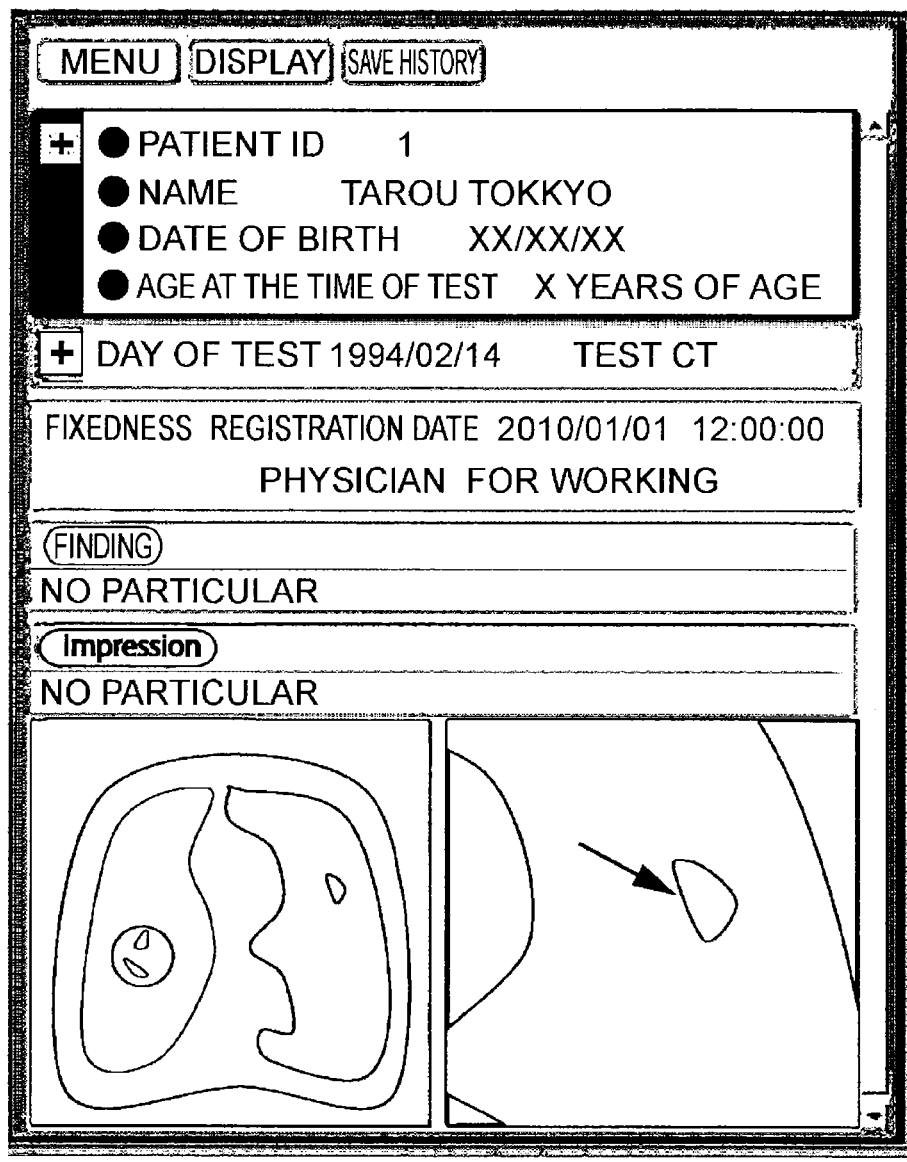
[FIG. 4F] It is a schematic diagram illustrating an outline of a medical image and an expanded image to be displayed with the diagnostic report.

A first example of the display modes is described with reference to FIG. 4F. As shown in FIG. 4F, the display controller (not shown) of the PC terminal causes the expanded image and the source medical image to be displayed side by side on an image display region in the diagnostic report, based on the information correlated therewith. Not limited to the example in FIG. 4F, the display sizes of the expanded image and the source medical image may be different from each other. Further, when the correlating part 424 configures the diagnostic report to vary the display sizes of the expanded image and the source of the medical image, these sizes may be changed by using an operating part and the like. The display order of the expanded mage and the source medical image is followed the layout of the diagnostic report, and not limited to the example in FIG. 4F.

Second Example

Figure 4G:
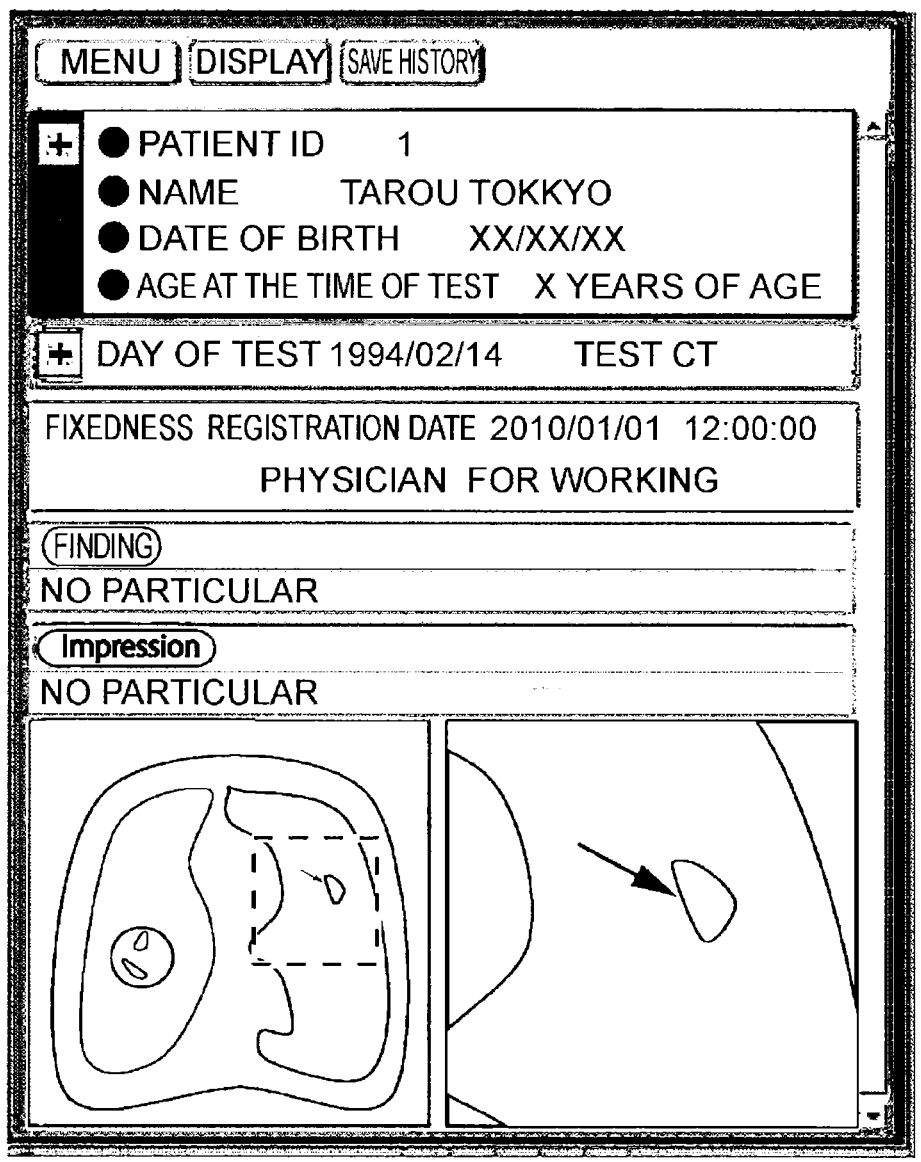
[FIG. 4G] It is a schematic diagram illustrating an outline of a medical image and an expanded image to be displayed with the diagnostic report.
Figure 4H:
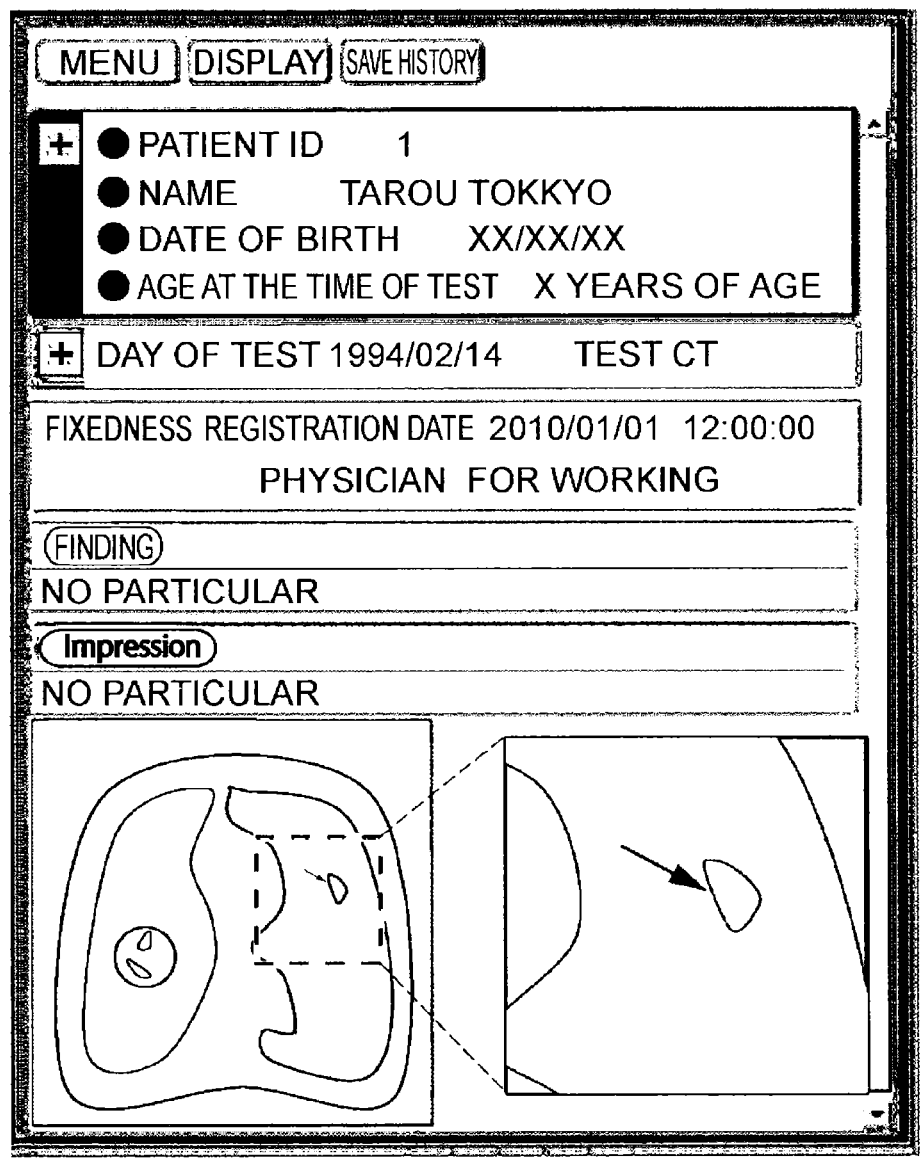
[FIG. 4H] It is a schematic diagram illustrating an outline of a medical image and an expanded image to be displayed with the diagnostic report.

A second example of the display modes is described with reference to FIG. 4G and FIG. 4H. As shown in FIG. 4G, the PC terminal causes the expanded image and the source medical image to be displayed side by side in the image display region of the diagnostic report, based on the information correlated therewith. Further, in the second example, the positional information indicating the expanded image position is displayed in the source medical image to be displayed.

For example, the display controller of the PC terminal refers supplementary information of the expanded image and the like, and extracts the positional information (coordinate information, and the like), which corresponds to the expanded image in the source medical image, from the supplementary information. Further, the display controller specifies, in the source medical image, a region corresponding to the expanded image, based on the extracted positional information. The display controller may specify only the outer edge positional information of the region corresponding to the specified expanded image. Furthermore, in the source medical image, the display controller makes the display mode for the region corresponding to the expanded image different from the display mode for the circumference thereof, based on the specified expanded image positional information.

For example, as shown in FIG. 4G, for the image data of the source medical image, the display controller implements drawing processing for drawing an outer edge of the region corresponding to the expanded image with a broken line. Further, as other example, the display controller implements processing which makes the region corresponding to the expanded image distinguishable by making the display color of the region different from the others'. Furthermore, as other example, the display controller implements processing for inversing the gradation display for the region corresponding to the expanded image to the gradation display for the others. Also, as other example, the display controller implements processing which makes the visibility of the region corresponding to the expanded image distinguishable by making the visibility of the region different from the others'.

Another example is described with reference to FIG. 4H. For the image data of the source medical image, the display controller draws the outer edge of the region corresponding to the expanded image with a real line, a broken line, and the like. The display controller also implements processing for drawing a line connecting the outer edge of the region corresponding to the expanded image and the outer edge of the expanded image (balloon display processing).

Third Example

Figure 4I:
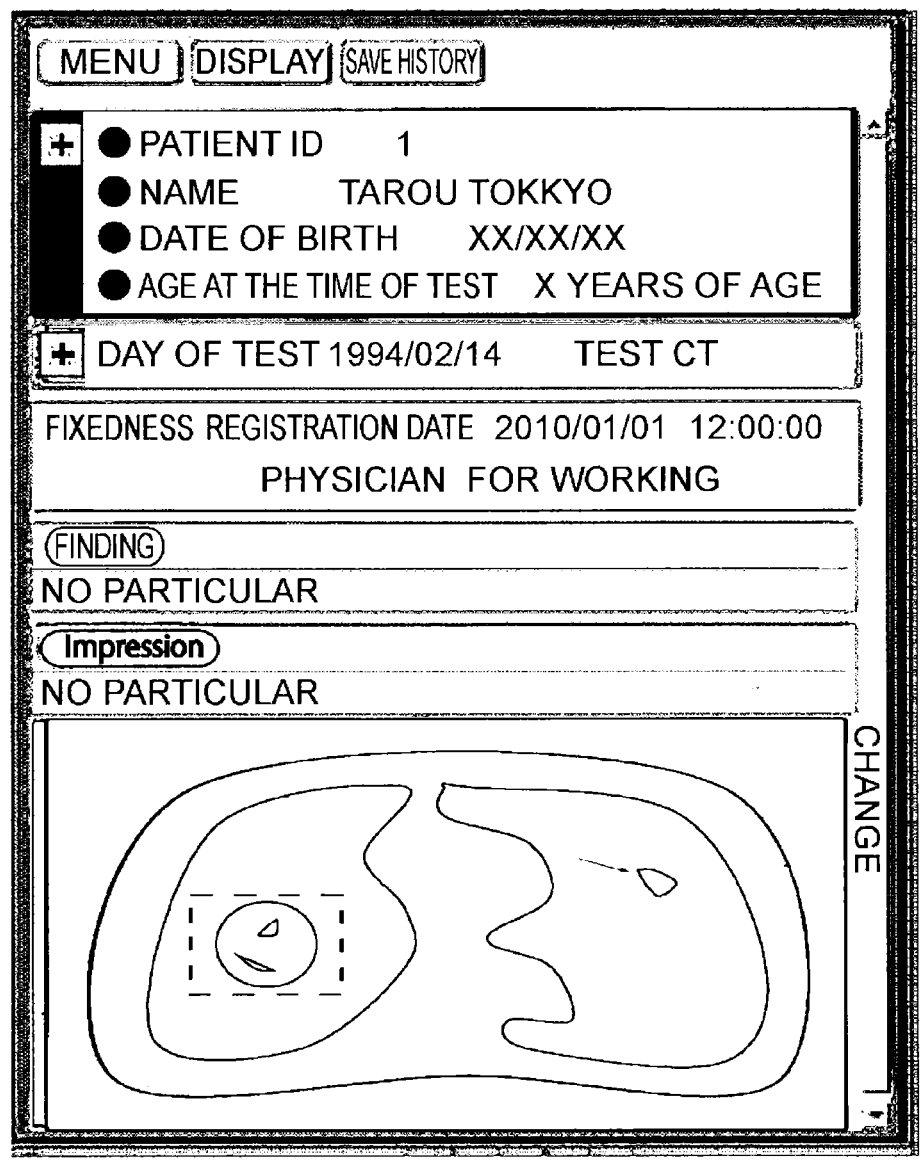
[FIG. 4I] It is a schematic diagram illustrating an outline of a medical image and an expanded image to be displayed with the diagnostic report.
Figure 4J:
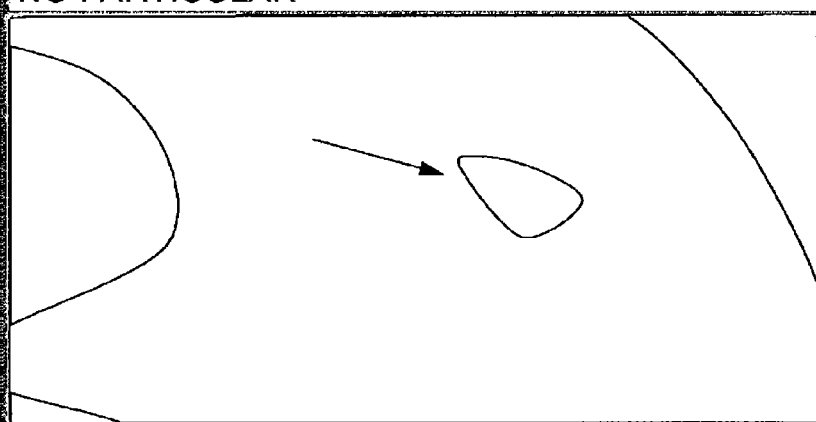
[FIG. 4J] It is a schematic diagram illustrating an outline of a medical image and an expanded image to be displayed with the diagnostic report.

A third example of the display modes is described with reference to FIG. 4I and FIG. 4J. As shown in FIG. 4I and FIG. 4J, based on the information correlated with the diagnostic report, the PC terminal causes either the expanded image or the source medical image to be selectively displayed in the image display region of the diagnostic report. For example, the display controller causes a switching button to be displayed in the diagnostic report, as shown in FIG. 4I and FIG. 4J. When an operation of switching the button is performed via the operation part of the PC terminal or the like, the display controller implements switching processing for switching the display from the source medical image to the expanded image (from FIG. 4I to FIG. 4J). Similarly, when the operation of switching the button is performed via the operation part of the PC terminal or the like, the display controller implements switching processing for switching the display from the source medical image to the expanded image (from FIG. 4J to FIG. 4I).

When there is a plurality of expanded images correlated with the diagnostic report, the display controller displays each of the expanded image file names and the like and each of the source medical image file names, instead of the switching button. Further, when an operation of selecting one of file names is performed via the operation part of the PC terminal or the like, the display controller implements processing for displaying the image having the file name corresponding to the operation.

This example and the first example may be combined. For example, based on the information correlated with the diagnostic report, the display controller causes one or more images among the plurality of expanded images to be displayed with the source medical image side by side. The display controller also causes the expanded image file names to be selectably displayed in the image display region of the diagnostic report. Further, when the operation of selecting one of file names is performed via the operation part of the PC terminal or the like, the display controller implements processing for displaying the expanded image having the file name corresponding to the operation with the source medical image side by side.

This example and the second example may also be combined. For example, based on the information correlated with the diagnostic report, the display controller causes one or more images among the plurality of expanded images to be displayed with the source medical image side by side. The display controller also implements processing for making the display mode for each of the expanded image positions in the source medical image (see the following fourth example) different from the display mode for the circumference thereof. Further, when an operation of selecting any of the expanded images from the source medical image is performed via the operation part of the PC terminal or the like, the display controller implements processing for displaying the expanded image corresponding to the position according to the operation with the source medical image side by side.

Fourth Example

Figure 4K:
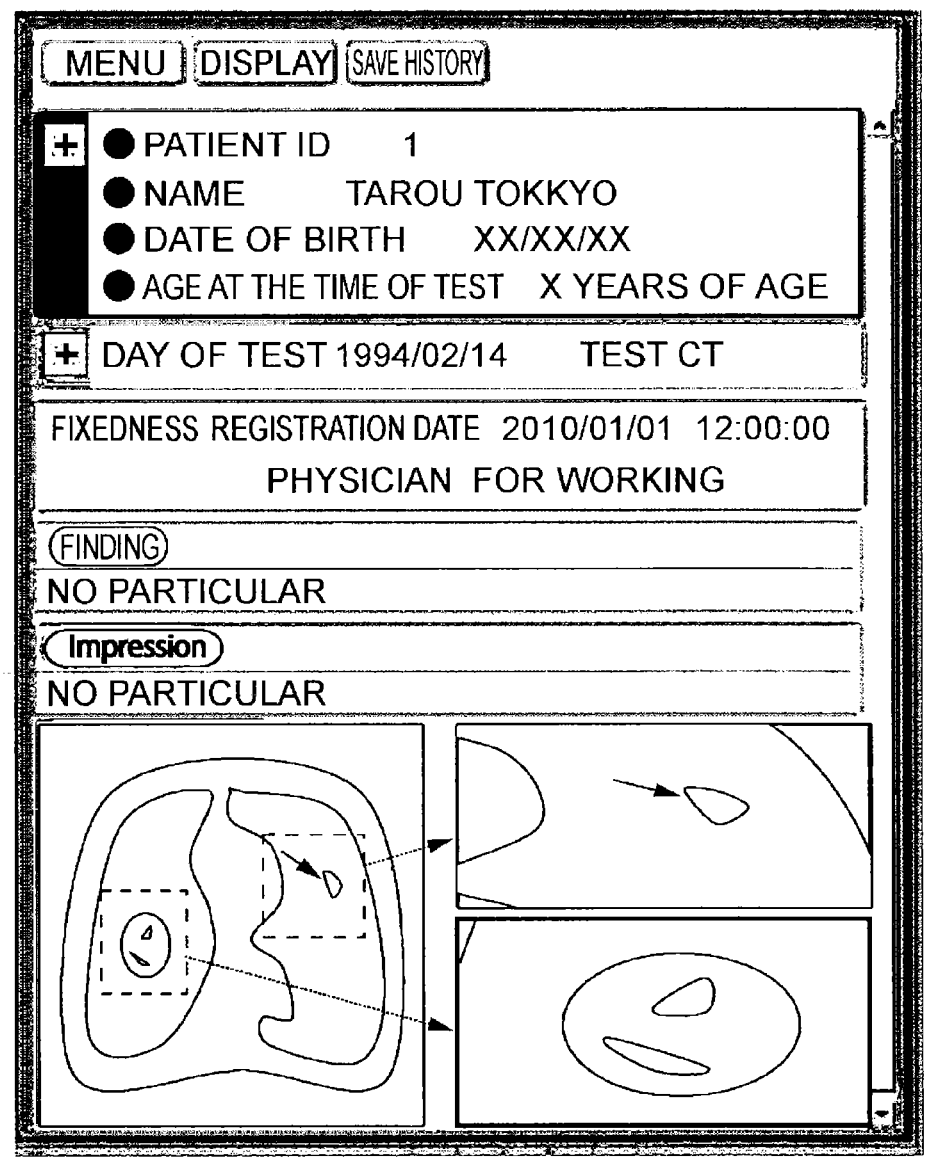
[FIG. 4K] It is a schematic diagram illustrating an outline of a medical image and an expanded image to be displayed with the diagnostic report.

A fourth example of the display modes is described with reference to FIG. 4K. As shown in FIG. 4K, the PC terminal causes the plurality of expanded images and the source medical image to be displayed side by side on the image display region of the diagnostic report, based on the information correlated therewith. It is not necessary for the display controller to display all of the plurality of expanded images with the source medical image side by side, but implement processing for displaying a number of expanded images in accordance with a setting and the source medical image side by side.

Fifth Example

A fifth example of the display modes is described. The PC terminal causes the plurality of expanded images and the source medical image to be displayed side by side on the image display region of the diagnostic report, based on the information correlated therewith. The display controller also causes a button for performing non-display processing of the expanded image to be displayed somewhere on image in which the diagnostic report is displayed. Further, when the operation of selecting the button is performed via the operation part of the PC terminal or the like, the display controller implements processing for displaying only the source medical image on the image display region, and not displaying any of the expanded images. In a case that the expanded images are non-displayed, the display region for the source medical image may be expanded.

Sixth Example

Figure 4L:
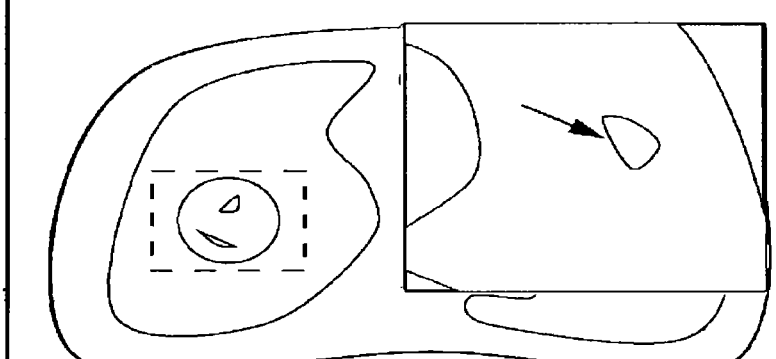
[FIG. 4L] It is a schematic diagram illustrating an outline of a medical image and an expanded image to be displayed with the diagnostic report.

A sixth example of the display modes is described with reference to FIG. 4L. As shown in FIG. 4L, the PC terminal causes the expanded image superposed on the source medical image to be displayed on the image display region of the diagnostic report, based on the information correlated therewith. This sixth example and the third example above may be combined. As shown in FIG. 4L, the display controller causes the switching button to be displayed in the image display region of the diagnostic report, based on the information correlated therewith. When the operation of selecting the switching button is performed via the operation part of the PC terminal or the like, the display controller implements processing for displaying only the source medical image on the image display region, and not displaying the expanded image.

When there is a plurality of expanded images correlated with the diagnostic report, the display controller causes each of the expanded image file names and the like and each of the source medical image file names to be displayed, instead of the switching button. Further, when the operation of selecting one of file names is performed via the operation part of the PC terminal or the like, the display controller implements processing for displaying the image having the file name corresponding to the operation.

Further, as other examples described above, the display controller may cause the positions corresponding to each of the expanded images to be displayed on the source medical image (see FIG. 4K), and implement processing for displaying while superposing only the selected expanded image on the source medical image and not displaying the other expanded images, in accordance with the operation of selecting any of the positions.

As described above, utilizing the display modes corresponding to the diagnostic report, the expanded image, and the source medical image, it is possible to reserve the display region even if the display region is limited to the display of the PC terminal of the test requesting doctor and the like. It is also possible to clarify the positional relationship between the source medical image and the expanded image.

Operation/Effect

Operations and effects of the report generation apparatus 4 according to the first embodiment are described.

The report generation apparatus 4 specifies a predetermined region in the medical image displayed on the display 43. The report generation apparatus 4 also generate an image of a predetermined range including the region. For example, the report generation apparatus 4 generates an expanded image corresponding to the predetermined range.

The predetermined region is specified, for example, by the specifying par 423b, based on a shape drawn on the medical image. This shape may be an arrow pointing an attention site, or a shape surrounding the attention site, in the medical image. This shape includes at least any of shapes, such as a circle, an ellipse, a polygon, and a shape drawn freehand. Also, in order to generate the expanded image, a predetermined range including a predetermined position in the medical image may be extracted. In a case that the shape is an arrow, the extracting part 423c extracts an image of a predetermined range including a tip-point of the arrow. Further, in a case that the shape is a shape surrounding the attention site, the extracting part 423c specifies the shape as an image region to extract an image of a predetermined range. The following is an example of extracting processing. The specifying part 423b detects the circumference of an annotation which is added to the medical image. The specifying part 423b then specifies the circumference and the part within the circumference as an image region. The extracting part 423c determines a shape circumscribing to the specified image region. The extracting part 423c then specifies the shape as a predetermined range, and extracts the specified range from the medical image.

As described above, the report generation apparatus 4 automatically extracts an image of a predetermined range including a specified image region from the medical image, and expands the extracted image. According to such the configuration, it is not necessary for the physician to generate expanded images every time a diagnostic report is generated. Therefore, the physician can generate a diagnostic report by only selecting an arbitrary image from the expanded images and implementing an operation for correlating the selected image to the finding input field. That is, it is possible to generate the diagnostic report easily by the report generation apparatus 4 according to the present embodiment.

Further, in the present embodiment, the correlating part 424 can correlate the expanded image and the medical image which is the source of the expanded image, with the diagnostic report.

For example, if the diagnostic report is correlated with not only the expanded image but also the medical image, it is possible for the doctor and the like who later confirm the diagnostic report to easily understand that the expanded image is corresponded to which part of the medical image.

Modified Examples

A method for specifying an image region is not limited to the method described in the first embodiment. That is, it is not limited to the configuration in which an image region is specified based on an annotation.

Modified Example 1

Figure 6:
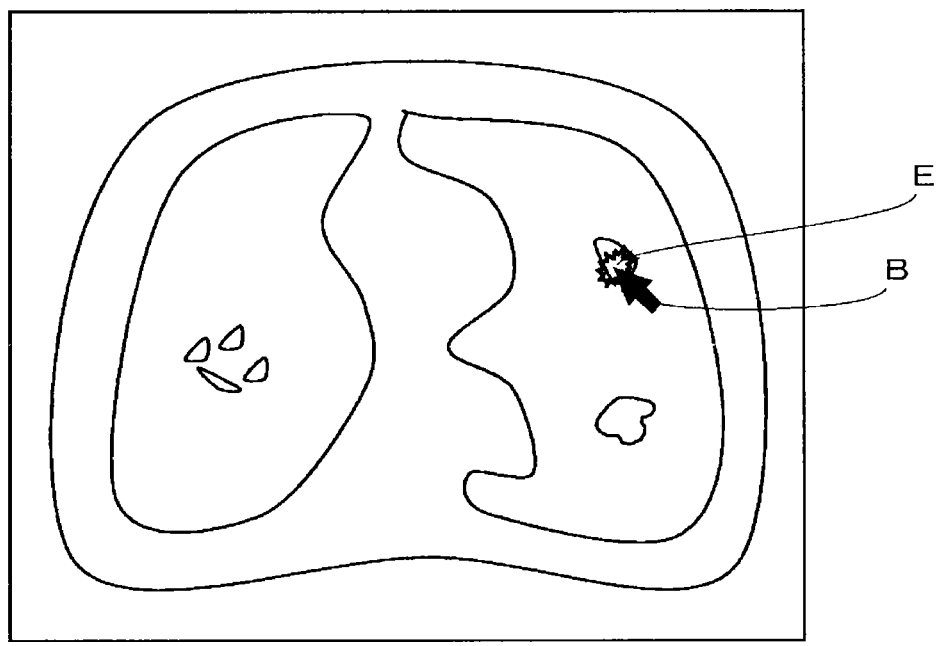
[FIG. 6] It is a diagram illustrating an example of medical images according to a modified example.

For example, it is possible for the specifying part 423b to specify an image region, based on a drag operation by the operator using the input part 41, such as a mouse. That is, without implementing the operation for adding a shape display, such as an annotation for specifying an attention site, and the like, the physician and the like perform a drag operation while designating the attention site using the input part 41 or the like, such as a mouse pointer. Thereby, the specifying part 423b specifies the attention site as an image region including a designated point designated by the drag operation. A specific example of this process is described with reference to FIG. 6. FIG. 6 is a diagram illustrating an example of medical images according to a modified example. In FIG. 6, in order to easily find the designated point when the drag operation is performed by the operator, a partially expanded diagram is also shown.

The physician either operates a pointer B displayed on a medical image by using a mouse to designate the attention site, or performs the drag operation to include the attention site. The specifying part 423b specifies a designated point E as the image region. Otherwise, the specifying part 423b specifies a plane designated through the drag operation as the image region. After that, based on the image region, the extracting part 423c or the like implements the similar processes as the above embodiment, such as extraction of a predetermined range, and generation of expanded images. By these processing, it is possible to display the expanded image including the designated point E or plane on the display 43.

In the modified example 1, it is possible to specify an attention site to generate an expanded image without implementing the operation for adding an annotation for the source medical image by the physician and the like.

Modified Example 2

Otherwise, it is possible for the specifying part 423b to specify the attention site designated in the medical image as the image region.

Specifically, an analyzing part, not shown, implements image analysis on the medical image displayed on the display 43. The analyzing part acquires positional information of an attention site of a lesion site or the like by the image analysis. The analyzing part designates the attention site by the above process. The specifying part 423b determines the region of the attention site, based on the designated attention site positional information. The specifying part 423b then specifies the determined region as an image region. After that, based on the image region, the extracting part 423c or the like implements the similar processes as the above embodiment, such as extraction of a predetermined range, and generation of expanded images. It is possible to display the expanded image including the attention site designated by those processes.

For either the modified example 1 or the modified example 2, it is possible to automatically extract and expand the image of the predetermined range including the image region. According to such the configuration, it is not necessary for the physician to generate expanded images every time a diagnostic report is generated. Therefore, the physician can generates a diagnostic report by only selecting an arbitrary image from the expanded images and correlating the selected image with the finding input field. That is, it is possible for the diagnostic report generating work to be done easily.

Second Embodiment

Next, configurations of a report reading apparatus 6 according to a second embodiment are described with reference to FIG. 7 to FIG. 9. Detail descriptions of the same configurations as that of the first embodiment may be omitted.

Whole Configuration of Medical Information System 1

Figure 7:
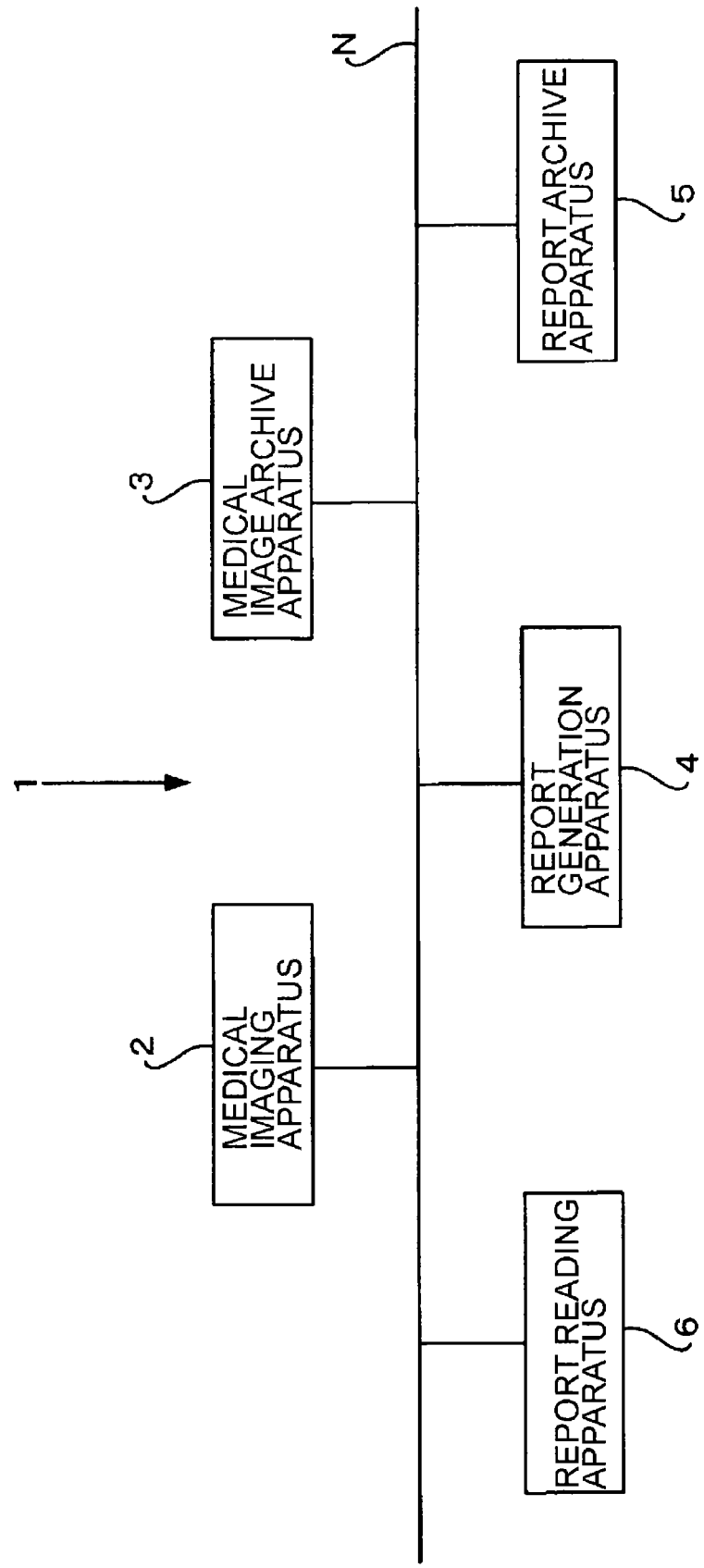
[FIG. 7] It is an overall view of a medical information system according to a second embodiment.

As shown in FIG. 7, the medical information system 1 comprises the medical imaging apparatus 2, the medical image archive apparatus 3, the report generation apparatus 4, the report archive apparatus 5, and a report reading apparatus 6.

The report reading apparatus 6 is an apparatus for reading the diagnostic report generated by the report generation apparatus 4. Hereinafter, detail descriptions of the report reading apparatus 6 is described.

Configuration of Report Reading Apparatus

Figure 8:
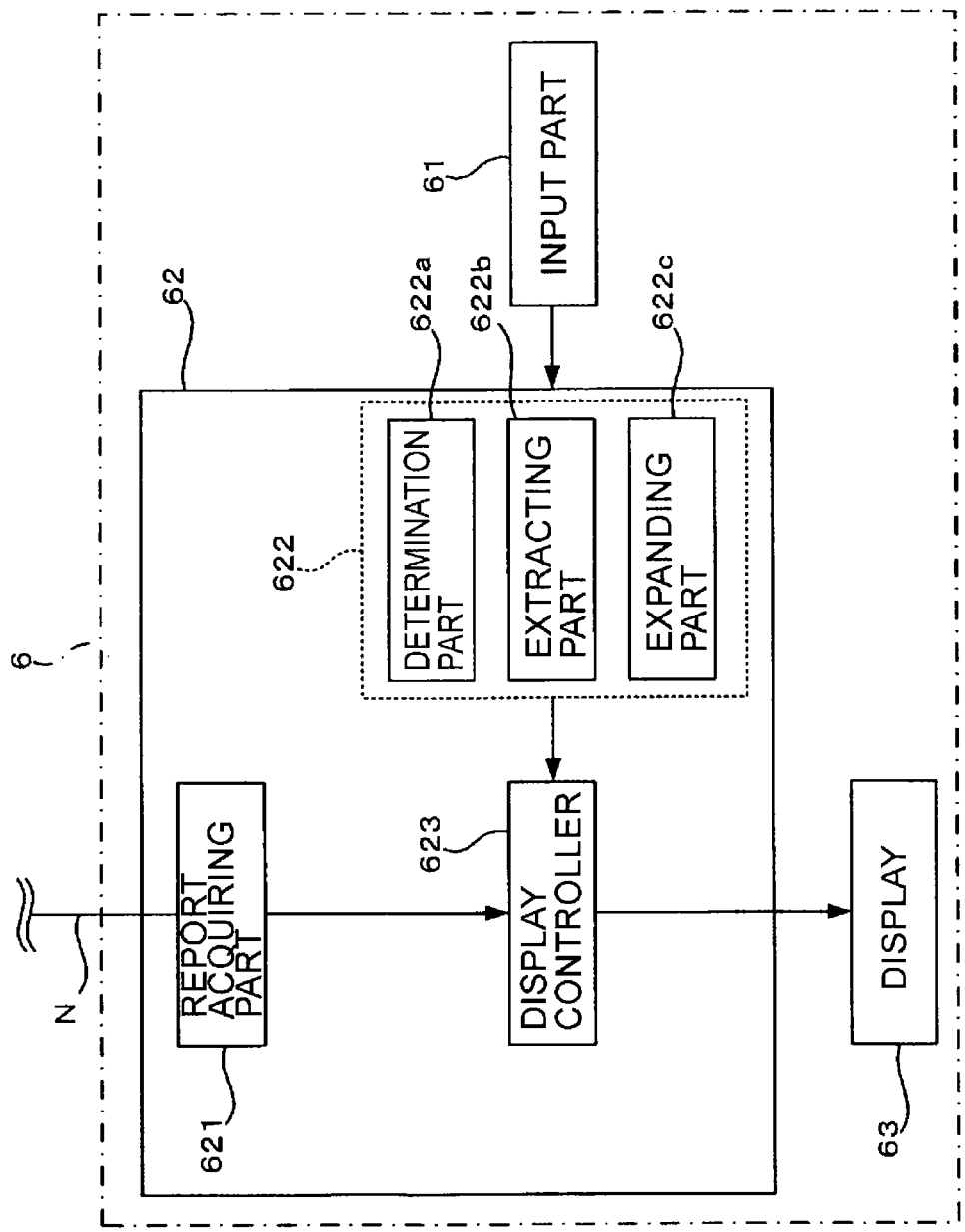
[FIG. 8] It is a diagram illustrating a report reading apparatus according to the second embodiment.
Figure 9:
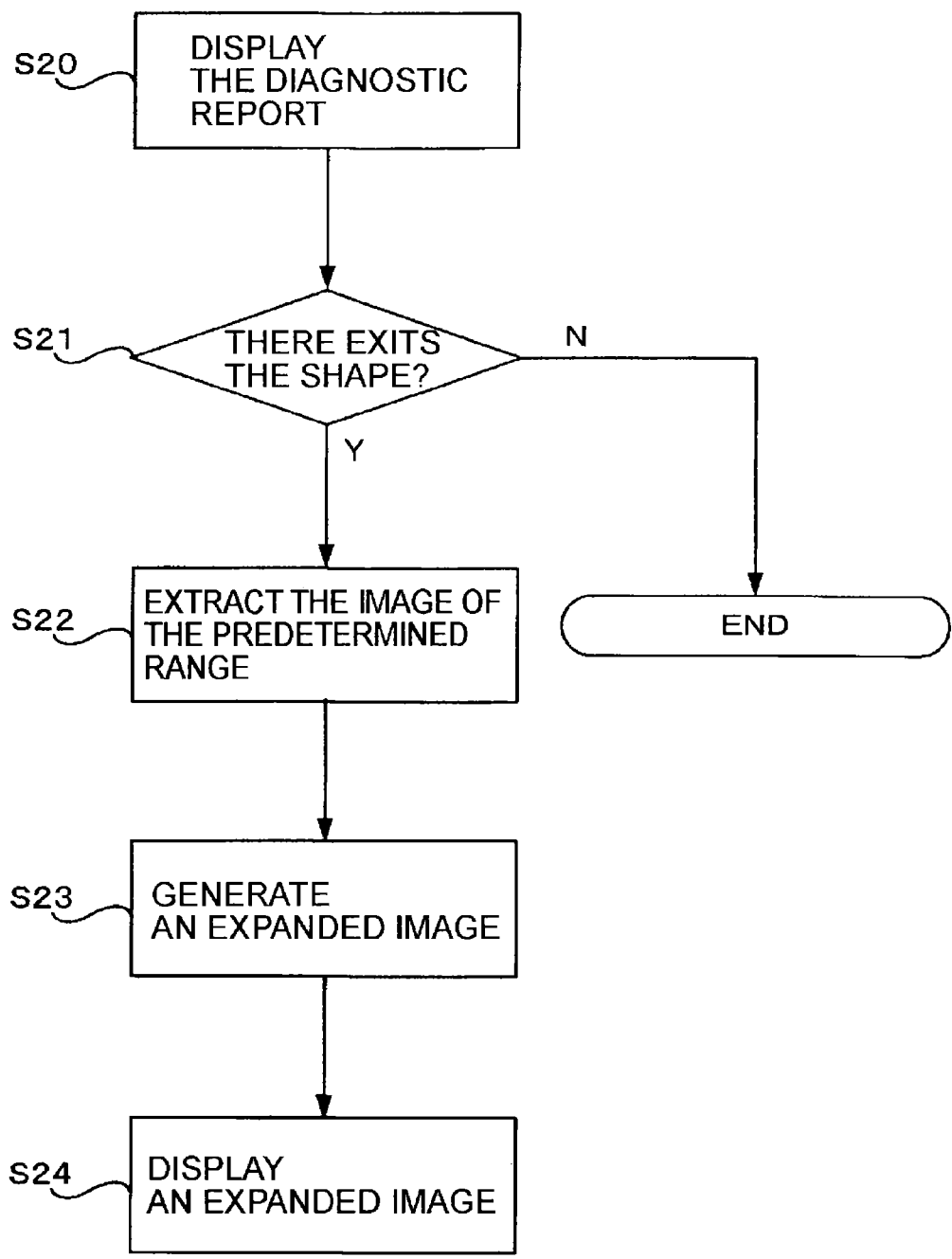
[FIG. 9] It is a flowchart illustrating an operation of the report reading apparatus according to the second embodiment.

FIG. 8 is a block diagram illustrating the detail descriptions of the report reading apparatus 6 according to the present embodiment. The report reading apparatus 6 comprises an input part 61, a CPU 62, and a display 63.

Input Part

The input part 61 is used for instructing a various instructions of the report reading apparatus 6. The input part 61 may be, for example, a keyboard, a mouse, a trackball, a joystick, or the like. As the input part 61, GUI displayed on the display 63 may also be used.

CPU

In the present embodiment, the CPU 62 functions as a report acquiring part 621, a processer 622, and a display controller 623.

Based on the instruction from the input part 61 or the like, the report acquiring part 621 acquires diagnostic reports from the report archive apparatus 5. The diagnostic reports are referred by the doctor and the like. Specifically, when a patient ID is input via the input part 61, the report acquiring part 621 reads the diagnostic report corresponding to the patient ID out from the report archive apparatus 5.

The processor 622 implements various kinds of processing on either one or both of the diagnostic report acquired by the report acquiring part 621 and the medical image correlated therewith. The processor 622 in the present embodiment comprises a determination part 622a, an extracting part 622b, and an expanding part 622c.

The determination part 622a determines whether the medical image correlated with the diagnostic report includes a shape indicating an attention site. Specifically, the determination part 622a implements edge detection processing or the like on the medical image to determine whether the shape (annotation or the like) is added or not. When a plurality of medical images is correlated with the diagnostic report, the determination part 622a implements the above processing on each of the plurality of medical images. The determination part 622a may start the processing by the instruction via the input part 61 or the like (manually). Otherwise, the determination part 622a may start the processing automatically in response to the acquisition of the diagnostic report by the report acquiring part 621.

When the determination part 622a determines that there is the shape indicating the attention site in the medical image, the extracting part 622b extracts an image of a predetermined range including at least a part of the shape. Specifically, in a case that a circle annotation is added to the medical image correlated with the diagnostic report is described. Firstly, the extracting part 622b determines a rectangle circumscribing to the circle annotation. Next, the extracting part 622b determines a range expanded by a predetermined length evenly from each vertex of the rectangle, and specifies an image of the range as a predetermined range. Lastly, the extracting part 622b extracts the image of the predetermined range by trimming. When a plurality of shapes is added to the medical image correlated with the diagnostic report, the extracting part 622b implements the above processing for each of the shapes. Further, when the rectangle including a part of the annotation is designated by the instruction via the input part 61 or the like, it is possible for the extracting part 622b to extract the image of the predetermined range including a part of the annotation by implementing the above processing on the rectangle.

The expanding part 622c generates an expanded image corresponding to the image extracted by the extracting part 622b. The generated expanded image is displayed on the display 63. A specific example of the process by the expanding part 622c is the same as that of the expanding part 423d in the first embodiment.

The display controller 623 implements display control for the display 63. For example, the display controller 623 controls for displaying the expanded image expanded by the expanding part 622c on the display 63.

Display

The display 63 is a display to display a diagnostic report.

The report reading apparatus in the present embodiment may include at least the determination part 622a, the extracting part 622b, the expanding image 622c, the display controller 623, and the display 63, among the above configuration.

Operation

Next, operations of the report reading apparatus 6 according to the present embodiment are described with reference to FIG. 9.

Firstly, the report reading apparatus 6 is activated by the operator. The doctor and the like then input a patient ID using the input part 61. When the patient ID is input, the report acquiring part 621 acquires a diagnostic report correlated with the patient ID from the report archive apparatus 5. The display controller 623 causes the display 63 to display the acquired diagnostic report (S20).

The determination part 622a determines whether a shape indicating an attention site in the medical image correlated with the diagnostic report display in S20 exists or not (S21).

When it is determined that there exits such the shape (S21; Y), the extracting part 622b generates a rectangle circumscribing to the shape. The extracting part 622b then designated the range expanded by a predetermined length evenly from each vertex of the rectangle, as a predetermined range. Further, the extracting part 622b extracts an image of the predetermined range by trimming (S22). When it is determined that there exists no shape therein (S21; N), the processes after S22 are not implemented.

The expanding part 622c generates an expanded image corresponding to the image extracted in S22 (S23). When a plurality of shapes indicating the attention site exists in the medical image, the processes of S22 and S23 are implemented on each of the shapes.

The display controller 623 causes the display 63 to display the expanded image generated in S23 (S24).

Operation/Effect

Operations and effects of the report reading apparatus 6 according to the second embodiment are described.

The report reading apparatus 6 in the present embodiment comprises the display 63, the determination part 622a, the extracting part 622b, the expanding part 622c, and the display controller 623. The display 63 displays a diagnostic report correlated with a medical image. The determination part 622a determines whether there exists a shape indicating an attention site in the correlated medical image. When it is determined that there exists the shape indicating the attention site, the extracting part 622b extracts an image of a predetermined range including at least a part of the shape. The expanding part 622c generates an expanded image corresponding to the extracted image. The display controller 623 causes the display 63 to display the expanded image.

As described above, the report reading apparatus 6 automatically extracts and expands the image of the predetermined range including the attention site in the medical image correlated with the diagnostic report. According to such the configuration, it is possible for the doctor and the like to easily interpret the diagnostic report. In addition, it is not necessary for the physician to generate expanded images every time a diagnostic report is generated. Therefore, the physician can generates a diagnostic report by only correlating the medical image, which is a source of findings, with the finding input field. That is, according to the report reading apparatus of the present embodiment, it is also possible to do easily the diagnostic report generating work.

Third Embodiment

Next, configurations of the report generation apparatus 4 according to a third embodiment are described. Detail descriptions of the same configurations as that of the first embodiment may be omitted.

In the third embodiment, the processes from FIG. 3A to FIG. 3D in the first embodiment, that is, the processes of S10 to S14 in the flowchart in FIG. 5 is the same as that of the first embodiment. S10 is the display process for displaying a diagnostic report generating screen, and S14 is the process for extracting a predetermined range from a source medical image.

The report generating apparatus 4 according to the third embodiment comprises a segment image generator (not shown) for generating a segment image without changing the display magnification of the extracted image. The display controller 425 causes the display 43 to display the generated segment image. The physician performs an instruction to correlate the displayed segment image with a diagnostic report via the input part 41 (same as in FIG. 3F). Based on the instruction, the correlating part 424 correlates the generated segment image with the diagnostic report (same as in FIG. 3G). The diagnostic report correlated with the segment image is generated, based on such the processes.

There may be a case that the diagnostic report is correlated with the information related to the arranging positions and the display modes of the expanded image and the source medical image in the image display field of the diagnostic report. Based on the correlated information, for example, the segment image and the source medical image are displayed with the diagnostic report in the PC terminal used by the test requesting doctor and the like, same as the example of each display mode in the first embodiment.

Operation/Effect

Operations and effects of the report generation apparatus 4 according to the third embodiment are described.

The report generation apparatus 4 specifies a predetermined region in the medical image displayed on the display 43. The report generation apparatus 4 also generates a segment image of a predetermined range including the region.

The predetermined region is specified, for example, by the specifying part 423b, based on a shape drawn in the medical image. Also, in order to generate an expanded image, there may be a case that a predetermined range including a predetermined position in the medical image is extracted. Further, when the shape is a shape surrounding an attention site, the extracting part 423c specifies the shape as an image region to extract an image of the predetermined range.

In this way, the report generation apparatus 4 automatically extracts the image of the predetermined range including the image region extracted from the medical image, and generates a segment image of the extracted region. According to such the configuration, it is not necessary for the physician to generate segment images every time a diagnostic report is generated. Therefore, the physician can generate a diagnostic report by only selecting an arbitrary image from the segment image and implementing the operation for correlating the selected image with the finding input field. That is, it is possible for the diagnostic report generating work to be done easily by the report generation apparatus 4 according to the present embodiment.

Further, in the present embodiment, it is possible for the correlating part 424 to correlate the segment image and the medical image which is the source thereof with the diagnostic report.

For example, if the diagnostic report is correlated with not only the segment image but also the medical image, it is possible for the doctor and the like who later confirm the diagnostic report to easily understand that the segment image is corresponded to which part of the medical image.

Common Effect of Embodiments

According to at least any one of embodiments described above, an image of a predetermined range of a medical image can be automatically extracted. According to such the configuration, it is not necessary for the physician to generate expanded images or segment images of the medical image correlated with the diagnostic report. That is, it is possible for the diagnostic report generating work to be done easily.

What is claimed is:

1. A report generation support apparatus, comprising:
a specifying part configured to detect an annotation drawn in a first medical image, and configured to specify a region or a position of the annotation in the first medical image;
a generator configured to extract a segment image as a second medical image from the first medical image, the segment image including the region or the position specified by the specifying part; and
a display configured to display a diagnostic report, the first medical image, and the second medical image, wherein
the generator includes an extractor configured to extract a predetermined range that includes the region or position specified by the specifying part from the first medical image;
the annotation is a shape surrounding an attention site in the medical image; and
the extractor is configured to determine a rectangle circumscribing to the specified image region and a range expanded from each vertex of the rectangle, and extract the predetermined range as the specified region or position.

2. The report generation support apparatus according to claim 1, comprising,
a correlating part configured to correlate the second medical image with the diagnostic report.

3. The report generation support apparatus according to claim 2, wherein,
the correlating part is configured to correlate the diagnostic report with the first medical image and the second medical image.

4. The report generation support apparatus according to claim 3, wherein,
the correlating part is configured to embed link information to the diagnostic report in order to correlate each other.

5. The report generation support apparatus according to claim 2, wherein,
the correlating part is configured to embed link information to the diagnostic report in order to correlate each other.

6. The report generation support apparatus according to claim 1, comprising,
a correlating part configured to correlate image processing conditions for the second medical image with the diagnostic report.

7. The report generation support apparatus according to claim 6, wherein,
the correlating part is configured to embed link information to the diagnostic report in order to correlate each other.

8. The report generation support apparatus according to claim 1, wherein,
the generator is configured to generate an expanded image of the first medical image as the second medical image, based on the region or the position specified by the specifying part and the first medical image.

9. The report generation support apparatus according to claim 1, wherein,
the generator includes an extracting part configured to extract a predetermined range that includes the region or the position specified by the specifying part from the first medical image,
the annotation is an arrow pointing an attention site in the medical image, and
the extracting part is configured to extract the predetermined range including a tip-end region of the arrow.

10. The report generation support apparatus according to claim 1, comprising,
an input part configured to perform operations with respect to the first medical image; wherein
the specifying part is configured to specify the region, based on a drag operation using the input part.

11. The report generation support apparatus according to claim 1, comprising,
a display controller configured to display the first image and the second image side by side on the display.

12. The report generation support apparatus according to claim 11, wherein,
the display controller is configured to
control the display to display positional relationship information indicating a positional relationship between the first image and the second image.

13. The report generation support apparatus according to claim 12, wherein,
the positional relation information includes line information for displaying a line connecting a position corresponding to the second image in the first image and the second image displayed side by side with the first image, and
the display controller is configured to
specify a predetermined range including the region or the position specified in the first image, and
control the display to display line connecting a position corresponding to the second image in the first image and the second image, based on the line information.

14. The report generation support apparatus according to claim 12, wherein,
the display controller is configured to
specify positional information corresponding to the second image in the first image, and
cause the position of the second image in the first image, based on the position information, to be displayed in a mode at least different from that of the circumference of the position, to display the positional relationship information.

15. The report generation support apparatus according to claim 11, wherein,
in a case that there exists a plurality of the second images, the display controller is configured to display at least one of the second images side by side with the first image.

16. The report generation support apparatus according to claim 15 comprising,
an input part configured to perform operations with respect to display of the display; wherein
in a case that there exists a plurality of the second images, the display controller is configured to control at least one of the second images to be displayed side by side with the first image, in accordance with the operation of the input part.

17. The report generation support apparatus according to claim 16, wherein,
the display controller is configured to, when there exists a plurality of the second images,
display each position corresponding to each of the second images in the first image in a mode at least different from that of the circumference, and further
control at least one of the second images to be displayed side by side with the first image, in accordance with an operation for selecting any one of the positions via the input part.

18. The report generation support apparatus according to claim 1, comprising,
a display controller configured to display the second image superposing onto the first image.

19. The report generation support apparatus according to claim 18, comprising,
an input part configured to perform operations with respect to display of the display, wherein
the display controller configured to control so as not to display the second image on the display, in accordance with the operation of the input part.

20. The report generation support apparatus according to claim 18, comprising,
an input part configured to perform operations with respect to display of the display, wherein
in a case that there exists a plurality of the second images, the display controller is configured to control at least one of the second images to be superposed onto the first image and displayed, in accordance with the operation of the input part.

21. The report generation support apparatus according to claim 20, comprising,
an input part configured to perform operations with respect to display of the display, wherein
the second image is an expanded image expanded a predetermined range in the first image,
the display controller is configured to, when there exists a plurality of the second images,
display each position corresponding to each of the second images in the first image in a mode at least different from that of the circumference, and further
control at least one of the expanded images to be superposed onto the first image and displayed, in accordance with the operation for selecting any one of the positions via the input part.

22. The report generation support apparatus according to claim 1, comprising,
an input part configured to perform operations with respect to display of the display; and
a display controller configured to switch the first image or the second image to display any one of those images on the display, in accordance with the operation of the input part.

23. The report generation support apparatus according to claim 1, wherein,
the generator is configured to extract the segment image from the first medical image by trimming.

24. The report generation support apparatus according to claim 1, wherein,
the extractor is configured to determine the range expanded from each vertex of the rectangle with a predetermined value in advance.

25. The report generation support apparatus according to claim 1, wherein, the extractor is configured to determine the range expanded in accordance with a size of the specified region or position.

26. The report generation support apparatus according to claim 1, wherein, the extractor is configured to determine the range expanded from each vertex of the rectangle by a predetermined length evenly.

27. A report generation support apparatus, comprising,
- a determination part configured to determine whether an annotation indicating an attention site exists or not in the correlated first image,
- a generator configured to extract a segment image as a second medical image from the first medical image, based on the annotation indicating the attention site, when there exists the annotation indicating the attention site,
- a display controller configured to cause the display to display the second image; and
- a display configured to display a diagnostic report, the first medical image and the second medical image,
- the generator comprises an extracting part configured to extract the segment image including at least a part of the annotation from the first image, when there exists the annotation indicating the attention site.

28. The report generation support apparatus according to claim 27, wherein,
- the generator comprises an extracting part configured to extract a predetermined ranae including at least a part of the annotation from the first image, when there exists the annotation indicating the attention site, and
- the generator is configured to generate an expanded image corresponding to the predetermined range, as the second medical image.

29. The report generation support apparatus according to claim 27, wherein,
- the generator is configured to extract the segment image from the first medical image by trimming.

30. A report generation support apparatus, comprising:
- a specifying part configured to detect an annotation drawn in a first medical image, and configure to specify a region or a position of the annotation in the first medical image;
- a generator configured to extract a segmentation image as a second medical image from the first medical image, the segment image including the region or the position specified by the specifying part: and
- a display configured to display a diagnostic report, the first medical image, and the second medical image, wherein,
- the generator includes an extractor configured to extract a predetermined range that includes the region or the position specified by the specifying part from the first medical image;
- the annotation is an arrow pointing an attention site in the medical image; and
- the extractor is configured to determine an arrow annotation specifying the image region and a range expanded from a tip-end region of the arrow annotation, and extract the predetermined range including the tip-end region of the arrow annotation.

31. The report generation support apparatus according to claim 30, wherein,
- the extractor is configured to determine the range expanded from the tip-end region of the arrow annotation with a predetermined value in advance.

32. The report generation support apparatus according to claim 30, wherein, the extractor is configured to determine the range expanded from the tip-end region of the arrow annotation by a predetermined length evenly.

* * * * *